United States Patent [19]
Baron et al.

[11] Patent Number: 6,087,166
[45] Date of Patent: *Jul. 11, 2000

[54] TRANSCRIPTIONAL ACTIVATORS WITH GRADED TRANSACTIVATION POTENTIAL

[75] Inventors: Udo Baron, Theodor-Heuss-Str. 4, D-69181 St. Ilgen, Germany; Manfred Gossen, El Cerrito, Calif.; Hermann Bujard, Heidelberg, Germany

[73] Assignees: BASF Aktiengesellschaft, Ludwigshafen; Udo Baron, St. Ilgen, both of Germany

[*] Notice: This patent issued on a continued prosecution application filed under 37 CFR 1.53(d), and is subject to the twenty year patent term provisions of 35 U.S.C. 154(a)(2).

[21] Appl. No.: 08/888,080

[22] Filed: Jul. 3, 1997

[51] Int. Cl.$^7$ .............................. C12N 5/10; C12N 1/00; C12N 15/62; C12N 15/63
[52] U.S. Cl. ..................... 435/325; 435/243; 435/320.1; 435/410; 536/23.4
[58] Field of Search ........................... 536/23.4; 435/325, 435/410, 243, 320.1

[56] References Cited

U.S. PATENT DOCUMENTS

| | | |
|---|---|---|
| 4,833,080 | 5/1989 | Brent et al. . |
| 5,221,778 | 6/1993 | Byrne et al. . |
| 5,464,758 | 11/1995 | Gossen et al. . |
| 5,650,298 | 7/1997 | Bujard et al. . |
| 5,654,168 | 8/1997 | Bujard et al. . |

FOREIGN PATENT DOCUMENTS

| | | |
|---|---|---|
| WO 91/19784 | 12/1991 | WIPO . |
| WO 94/29442 | 12/1994 | WIPO . |
| WO 96/01313 | 1/1996 | WIPO . |
| WO 96/40946 | 12/1996 | WIPO . |

OTHER PUBLICATIONS

Baim, S.B., et al., (1991) "A chimeric mammalian transactivator based on the Iac repressor that is regulated by temperature and isopropyl βD–thiogalactopyranoside", *Proceedings of the National Academy of Science*, vol. 88, pp. 5072–5076.

Berger, Shelley et al., (1992) "Genetic Isolation of ADA2: A Potential Transcriptional Adaptor Required for Function of Certain Acidic Activation Domains", *Cell*, vol. 70, pp. 251–265.

Brent, R. et al. (1985) "A Eukaryotic Transcriptional Activator Bearing the DNA Specificity of a Prokaryotic Repressor" *Cell* 43:729–736.

Cress, Douglas et al., (1991) "Critical Structural Elements of the VP16 Transcriptional Activation Domain", *Science*, vol. 251, pp. 87–90.

Elliston, Jonathan, et al. (1990) "Superactive Estrogen Receptors", *Journal of Biological Chemistry* (1990), vol. 265, No. 20, pp. 11517–11521.

Goodrich, James et al. (1993) "Drosophila TAF$_{II}$40 Interacts with Both A VP16 Activation Domain and the Basal Transcription Factor TFIIB", *Cell*, vol. 75, pp. 519–530.

Gossen, Manfred et al., (1992) "Tight control of gene expression in mammalian cells by tetracycline–responsive promoters", *Proceedings of the National Academy of Science*, vol. 89, pp. 5547–5551.

Gossen, Manfred et al., (1993) "Control of gene activity in higher eukaryotic cells by prokaryotic regulatory elements", *TIBS*, vol. 18, No. 12, pp. 471–475.

Gossen, Manfred et al. (1994) "Inducible Gene Expression Systems For Higher Eukaryotic Cells" *Current Opinion in Biotechnology* vol. 5, pp. 516–520.

Gossen, M. et al. (1995) "Transcriptional Activation by Tetracyclines in Mammalian Cells", *Sicence*, vol. 268, pp. 1766–1769.

Hayes, Steven, et al. (1993) "Mapping of a Major Surface–Exposed Site in Herpes Simplex Virus Protein Vmw65 to a Region of Direct Interaction in a Transcription Complex Assembly", *Journal of Virology*, vol. 67, No. 2, pp. 852–862.

Labow, M.A., et al., (1990) "Conversion of the Iac Repressor into an Allosterically Regulated Transcriptional Activator for Mammalian Cells", *Molecular and Cellular Biology*, vol. 10, No. 7, pp. 3343–3356.

Regier, Jeffrey et al. (1993), "Pattern of Aromatic and Hydrophobic Amino Acids Critical For One Of Two Subdomains of the VP16 Transcriptional Activator", *Proc. Natl. Acad. Sci. USA*, vol. 90, pp. 883–887.

Sadowski, Ivan et al. (1988), "GAL4–VP16 Is An Unusually Potent Transcriptional Activator", *Nature*, vol. 335, pp. 563–564.

Seipel, K. et al., (1992) "Different Activation Domains Stimulate Transcription From Remote ('Enhancer') And Proximal ('Promoter') Positions", *The EMBO Journal*, vol. 11, No. 13, pp. 4961–496.

Silverman, Neal et al. (1994), "Yeast ADA2 Protein Binds To The VP16 Protein Activation Domain and Activates Transcription", *Proc. Natl. Acad. Sci. USA*, vol. 91, pp. 11665–11668.

(List continued on next page.)

*Primary Examiner*—Terry McKelvey
*Attorney, Agent, or Firm*—Lahive & Cockfield, LLP; Giulio A. DeConti, Jr.; Catherine J. Kara

[57] ABSTRACT

Transcriptional activators which differ in their activation potential by more than 3 orders of magnitude are provided. The transactivators are fusions between a DNA binding protein (e.g., a Tet repressor) and minimal transcriptional activation domains derived from Herpes simplex virus protein 16 (VP16). Substitution mutations at amino acid position 442 within the minimal VP16 domain provide transactivators with differing transactivation ability. Moreover, chimeric activation domains comprising both wild type and mutant minimal VP16 domains provide additional variants with differing transactivation ability. Various aspects of the invention pertain to nucleic acid molecules, vectors, host cells, fusion proteins, transgenic and homologous recombinant organisms and methods of regulating gene transcription.

25 Claims, 4 Drawing Sheets

OTHER PUBLICATIONS

Triezenberg, S.J. et al., (1988) "Functional dissection of VP16, the trans–activator of herpes simplex virus immediate early gene expression", *Genes & Development*, vol. 2, pp. 718–729.

Wang, Y. et al. (1994), "A Regulatory System For Use In Gene Transfer", *Proc. Natl. Acad. Sci. USA*, vol. 91, pp. 8181–8184.

Wang, Y. et al. (1997) "Ligand–Inductible And Liver–Specific Target Gene Expression In Transgenic Mice", *Nature Biotechnology*, vol. 15, pp. 239–243.

Wu, Tsuei–Ju et al. (1994) "Transcriptional Activation by Herpes Simplex Virus Type 1 VP16 In Vitro and Its Inhibition by Oligopeptides", *Molecular and Cellular Biology*, vol. 14, No. 5, pp. 3484–3493.

TRANSCRIPTIONAL ACTIVATORS WITH GRADED TRANSACTIVATION POTENTIAL

BACKGROUND OF THE INVENTION

The ability to regulate gene expression is desirable in a variety of situations, including in the production of recombinant proteins, in gene therapy, and in analyses of cell development and differentiation. A wide variety of gene regulation systems have been described, some of which stimulate gene expression in a constitutive manner and some of which stimulate gene expression in an inducible manner. A popular approach to regulating gene expression is to create a transcriptional activator fusion protein (also referred to herein as a "transactivator") which is composed of a DNA binding domain, which has specificity for a particular target DNA binding site, and a transcriptional activation domain. To regulate expression of a gene of interest, the gene is operatively linked to the target DNA binding site and then both the gene and an expression vector encoding the transactivator fusion protein are coexpressed in a host cell. Upon binding of the transactivator fusion protein to the target DNA binding site, expression of the gene of interest is stimulated.

A constitutive transcriptional activator is created in cases where the DNA binding domain binds to its target site constitutively (i.e., without the need for an inducing agent to regulate DNA binding). One example of such a constitutive transactivator is GAL4-VP16 (Sadowski, I. et al.(1988) Nature 335:563–564), composed of the yeast GAL4 DNA binding domain linked to the C-terminal region of herpes simplex virus virion protein 16 (Triezenberg, S. J. et al. (1988) Genes Dev. 2:718–729). In contrast, when the DNA binding domain only binds to its target site in the presence or absence of an inducing agent, an inducible transcriptional activator is created. Examples of such inducible transcriptional activators are TetR-VP16, composed of a bacterial Tet repressor linked to VP16 (which binds to tetO sequences in the absence, but not the presence of tetracycline) (Gossen, M., and Bujard, H. (1992) Proc. Natl. Acad. Sci. U.S.A 89, 5547–5551) and rTetR-VP16, composed of a mutated Tet repressor linked to VP16 (which binds to tetO sequences in the presence but not the absence of tetracycline) (Gossen, M., et al. (1995) Science 268, 1766–1769).

The C-terminal transcriptional activation domain of HSV VP16 has been used frequently as the activator component of transactivator fusion proteins because of its strong capacity to stimulate transcription in eukaryotic cells. It has been shown, however, that overexpression of transcription factors can result in "squelching" (Gill, G., and Ptashne, M. (1988) Nature 334, 721–724), which is seen as a consequence of titrating components of the transcriptional machinery from their respective intracellular pools. For VP16, which is one of the most potent transactivators known, it has been demonstrated that its overexpression, e.g. as a fusion protein with GAL4, is not tolerated by cells (Berger, S. L., et al. (1992) Cell 70, 251–265, Kelleher, R. J., et al. (1990) Cell 61, 1209–1215). Considering that VP16 interacts with a variety of essential components of the transcriptional machinery, including the adaptor/coactivator protein ADA2 in S. cerevisiae (Silverman, N., et al. (1994) Proc. Natl. Acad. Sci. U.S.A 91, 11665–11668) and its human homologue (Candau, R., et al. (1996) Mol. Cell Biol. 16, 593–602), with TFIIB (Lin, Y. S., et al. (1991) Nature 353, 569–571), TFIID (Stringer, K. F., et al. (1990) Nature 345, 783–786), TFIIH (Xiao, H., et al. (1994) Mol. Cell Biol. 14, 7013–7024) and dTAFII40 (Goodrich, J. A., et al. (1993) Cell 75, 519–530), this is not surprising. Gilbert and coworkers (Gilbert, D. M., et al. (1993) Mol. Cell. Biol 13, 462–472) have found a correlation between squelching and growth arrest which indicates that toxicity through squelching is a quantitative problem where the intracellular concentration and the strength of activation domains are crucial parameters.

Thus, while the potent transcriptional activation ability of VP16 makes it an attractive component for use in transactivator fusion proteins, in certain instances it may be desirable to have a fusion protein with a lower transcriptional activation potential than that provided by wild type VP16. Alternatively, in other situations, it may be desirable to have a fusion protein with an even higher transcriptional activation potential than that provided by wild type VP16. Accordingly, additional transactivator fusion proteins with graded transactivation potentials are needed.

SUMMARY OF THE INVENTION

This invention provides a panel of fusion protein transactivators which contain VP16-derived minimal activation domains and which possess a graded transactivation potential spanning more than 3 orders of magnitude. These transactivators have the advantage that they are tolerated in cells at high concentrations provide the ability to regulate levels of gene expression in a very precise manner.

One aspect of the invention pertains to nucleic acid molecules that encode the transcriptional activator fusion proteins of the invention. In one embodiment, the nucleic acid molecule encodes a fusion protein which activates transcription, the fusion protein comprising a first polypeptide comprising a DNA binding domain operatively linked to a second polypeptide comprising a transcriptional activation domain, wherein the transcriptional activation domain comprises at least one copy of a mutated acidic region of herpes simplex virus virion protein 16 (HSV VP16), the mutated acidic region consisting of amino acid positions 436 to 447 of HSV VP16 and having an amino acid substitution at position 442 as compared to wild type HSV VP16. The mutated acidic region of HSV VP16 can have, for example, the amino acid sequence of SEQ ID NO: 2 (in which the phenylalanine at position 442 of wild type VP16 has been mutated to glycine, referred to herein as VP16[G]). Alternatively, the mutated acidic region of HSV VP16 can have, for example, the amino acid sequence of SEQ ID NO: 3 (in which the phenylalanine at position 442 of wild type VP16 has been mutated to tyrosine, referred to herein as VP16[Y]).

In other embodiments, of the invention the transcriptional activation domain of the fusion protein is composed of two or more copies of the minimal activation domain of VP16, at least one of which has a mutation at position 442. For example, in one embodiment, the transcriptional activation domain comprises two copies of VP16[G] (having the amino acid sequence of SEQ ID NO: 4). In another embodiment, the transcriptional activation domain comprises, in the N-terminal to C-terminal direction, one copy of the wild type VP16 minimal activation domain (referred to as VP16 [F]) and one copy of VP16[G]) (having the amino acid sequence of SEQ ID NO: 5). In yet another embodiment, the transcriptional activation domain comprises, in the N-terminal to C-terminal direction, one copy of VP16[G] and one copy of VP16[F] (having the amino acid sequence of SEQ ID NO: 6). In yet another embodiment, the transcriptional activation domain comprises, in the N-terminal to C-terminal direction, one copy of VP16[F], one copy of VP16[G] and one copy of VP16[Y] (having the amino acid sequence of SEQ ID NO: 7). In still another embodiment, the transcriptional activation domain comprises, in the N-terminal to C-terminal direction, one copy of VP16[G], one copy of VP16[F] and one copy of VP16[Y] (having the amino acid sequence of SEQ ID NO: 8).

In another embodiment, a nucleic acid molecule of the invention encodes a fusion protein which activates transcription, the fusion protein comprising a first polypeptide comprising a DNA binding domain operatively linked to a second polypeptide comprising a transcriptional activation domain, wherein the transcriptional activation domain consists of three copies of an acidic region of herpes simplex virus virion protein 16 (HSV VP16), the acidic region consisting of amino acid positions 436 to 447 of HSV VP16 (SEQ ID NO: 1). That is, the fusion protein contains three copies of the wild type VP16[F] minimal activation domain.

In yet another embodiment, a nucleic acid molecule of the invention encodes a fusion protein which activates transcription, the fusion protein comprising a first polypeptide comprising a DNA binding domain operatively linked to a second polypeptide comprising a transcriptional activation domain, wherein the transcriptional activation domain consists of four copies of an acidic region of herpes simplex virus virion protein 16 (HSV VP16), the acidic region consisting of amino acid positions 436 to 447 of HSV VP16 (SEQ ID NO:1). That is, the fusion protein contains four copies of the wild type VP16[F] minimal activation domain.

The first polypeptide of the fusion protein encoded by the nucleic acid molecules can be essentially any DNA binding domain having specificity for a particular target DNA binding site. In a preferred embodiment, the first polypeptide is a Tet repressor. In another preferred embodiment, the first polypeptide is a mutated Tet repressor that binds to a tetO operator in the presence, but not in the absence, of tetracycline or a tetracycline analogue. In yet other embodiments, the first polypeptide GAL4, LexA, LacR or a steroid hormone receptor.

The nucleic acid molecules of the invention can be incorporated into recombinant vectors that allow for expression of the fusion protein in a host cell. Accordingly, other aspects of the invention pertain to vectors which carry the nucleic acid molecules of the invention and host cells into which such vectors have been introduced. Yet another aspect of the invention pertains to the transactivator fusion proteins encoded by the nucleic acid molecules of the invention.

To regulate gene expression using the transactivator fusion proteins of the invention, an expression vector encoding the fusion protein is introduced into a host cell that contains (or is modified to contain) a gene of interest operatively linked to the target DNA binding site for the fusion protein. Upon expression of the fusion protein, or upon expression of the fusion protein and in the presence or absence of an appropriate inducing agent, transcription of the gene of interest is stimulated. Accordingly, methods of regulating gene expression using the fusion proteins of the invention are also within the scope of the invention. Processes for producing and isolating proteins of interest using the regulatory system of the invention are also encompassed by the invention.

Nucleic acid encoding the fusion proteins of the invention also can be incorporated into transgenic organisms (either integrated randomly or at a predetermined location in the genome by, for example, homologous recombination). Accordingly, such organisms are also encompassed by the invention.

DESCRIPTION OF THE DRAWINGS

FIG. 2A is a mobility shift of TetR-[F] fusions. FIG. 2B is a mobility shift of fusions between TetR and [F], [G] and [Y] domains. Mock transfected cells contained vector DNA without a tTA encoding insert.

FIG. 3A shows extracts from pools of HeLa cells stably transfected with DNA encoding tTA, tTA2, tTA3 or tTA4, respectively, under the control of PhCMv. FIG. 3B shows analysis of individual clones producing tTA or tTA3. For the tTA lanes in FIG. 3B, lane 1 shows extract from X1/5 cells; lane 2 shows extract of the X1/6-tTA cell line in Table 2 and lane 3 shows extract of a clone picked from the tTA transfected HeLa cell pool described in FIG. 3A. For the tTA3 lanes in FIG. 3B, lanes 1 and 2 show extracts of tTA3 producing cell lines in Table 2 and lane 3 shows extract of a clone picked from the tTA3 producing HeLa cell pool described in FIG. 3A. (*) denotes a marker used for quantitation of the signals.

DETAILED DESCRIPTION OF THE INVENTION

Figure 1:
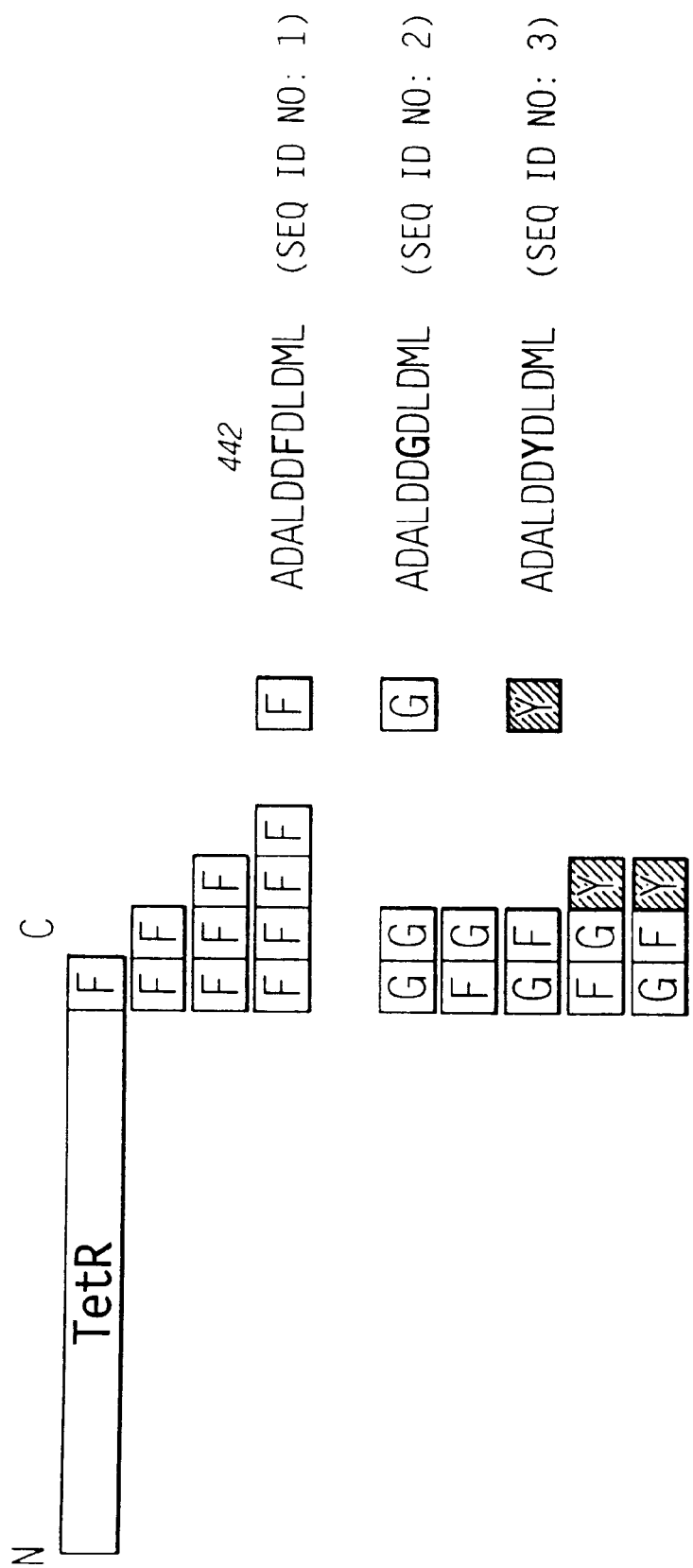
FIG. 1 is a schematic diagram of fusions between TetR and minimal acidic activation domains derived from VP16. The amino acid sequence of the domains is outlined at right: [F] (also shown as SEQ ID NO: 1) denotes the wild type sequence between position 436 and 447 of VP16 which contains a phenylalanine at position 442. In the mutated minimal domains [G] (also shown as SEQ ID NO: 2) or [Y] (also shown as SEQ ID NO: 3), Phe442 is substituted by glycine or tyrosine, respectively. Various combinations of the minimal domains were fused to TetR resulting in the panel of fusion proteins outlined at left.

In the following subsections, transactivator fusion proteins of the invention having graded transcriptional activation potentials are primarily described in the context of tetracycline-controlled transcription activation systems, as a representative example of a system using VP16-derived activation domains. However, as will be appreciated by the skilled artisan, the novel VP16-derived activation domains of the invention can be used in combination with other DNA binding domains, by applying the same approaches described herein for the tet system. Non-limiting examples of other DNA binding domains/proteins that have well characterized DNA binding specificities and that previously have been used in chimeric transactivator fusion proteins include GAL4 (see e.g., Sadowski, I. et al.(1988) *Nature* 335:563–564), LexA (see e.g., Brent R. and Ptashne M. (1985) *Cell* 43, 729–36), LacR (see e.g., Labow et al. (1990) *Mol. Cell. Biol.* 10:3343–3356; Baim et al. (1991) *Proc. Natl. Acad. Sci. USA* 88:5072–5076) and steroid hormone receptors (Ellliston, J. F. et al. (1990) *J. Biol. Chem.* 265, 11517–11521). Moreover, the components and methods of the current invention can be applied to the regulatory system described in Wang Y., et al. (1994) *Proc. Natl. Acad. Sci. USA* 9, 8180–8184, which utilizes a fusion of GAL4, a hormone receptor and VP16.

The tetracycline controlled transcription activation system has been described previously (Gossen, M., and Bujard, H. (1992) *Proc. Natl. Acad. Sci. U.S.A* 89, 5547–5551) and functions as an efficient genetic switch in a variety of eukaryotic cells including mammalian (Resnitzky, D., et al. (1994) *Mol. Cell. Biol* 14, 1669–1679), plant (Weinmann, P., et al. (1994) *Plant J* 5, 559–569) and yeast cells. It also allows to effectively control gene activities at the level of organisms as shown in plants (Weinmann, P., et al. (1994) Plant J 5, 559–569), mice (Kistner, A., et al. (1996) *Proc. Natl. Acad. Sci. U.S.A*. 93, 10933–10938) and Drosophila.

One of the key components of this tet system is the tetracycline controlled transactivator (tTA), the fusion protein between the repressor of the (Tn10) tetracycline resistance operon of *E. coli* and a C-terminal portion of VP16 that contains domains capable of activating transcription (Triezenberg, S. J., et al. (1988) *Genes Dev* 2, 718–729). In absence of the effector tetracycline (Tc), tTA will activate transcription from a suitably engineered minimal promoter by binding to an array of tet operator (tetO) sequences positioned upstream. In presence of Tc, tTA is prevented from binding to its target and thus transcription is abolished.

Using a TetR mutant, a transactivator with a reverse phenotype (rtTA) has been generated which, when compared to tTA, functions in the opposite fashion: it requires Tc derivatives like doxycycline (Dox) or anhydrotetracycline (ATc) for binding to its operator and thus activates transcription only in the presence but not in the absence of its effector. This system is referred to herein as the "reverse tet system" and the reverse transactivator is abbreviated as "rtTA". Transcriptional regulation via rtTA has been shown in mammalian cells (Gossen, M., et al. (1995) *Science* 268, 1766–1769) and in mice (Kistner, A., et al. (1996) *Proc. Natl. Acad. Sci. U.S.A*. 93, 10933–10938).

Further details on the tet and reverse tet systems are described in U.S. Pat. No. 5,464,758, U.S. Pat. No. 5,589, 362, PCT Publication WO 94/29442, PCT Publication, WO 96/01313 and PCT Publication WO 96/40892.

Despite their widespread application, the tet and reverse tet regulatory systems may still be further developed to fulfill specific experimental requirements. Although use of the VP16 activation domain has been associated in certain situations with "squelching" (see Background), we attribute the fact that tTA and rtTA have nevertheless been shown to function well in numerous systems to the exceptional specificity of the Tet repressor/operator interaction (Kleinschmidt, C., et al. (1988) *Biochemistry* 27, 1094–1104). This specificity warrants a high occupancy of tetO sequences by the transactivator at low intracellular concentrations of tTA/rtTA. Random integration of tTA/rtTA expression units into chromosomes then allows to screen for integration sites where the synthesis of tTA/rtTA is sufficiently high to yield good activation but low enough to prevent deleterious effects by squelching. For example, we estimate the concentration of tTA in our HeLa X1 cell line to be around 4000 molecules per cell (Gossen, M. (1993) Ph. D. Thesis, Univ. Heidelberg), hardly sufficient to seriously affect pools of basal transcription factors but nevertheless capable of activating a chromosomally integrated tTA responsive promoter more than $10^5$ fold. This cell line, like numerous others, as well as several tTA and rtTA producing mouse lines, are perfectly stable in our laboratory over several years, demonstrating that the respective intracellular concentrations of the transactivator lie within a "physiological" window.

There are, however, experimental strategies where screening or selection for an appropriate intracellular concentration of the transactivator is not possible. For example, to achieve cell type-specific regulation of a gene in transgenic organisms, it appears attractive to place—via homologous recombination—a tTA/rtTA gene under the control of the promoter which directs the expression of the gene of interest. Given the proper design of the vector used for recombination, the integration event will, at the same time, inactivate the target gene; its coding sequence controlled by a tTA/rtTA responsive promoter can be provided independently. While such an experimental "knock in/knock out" strategy would allow for cell type-specific expression of tTA/rtTA and thus for an equally specific Tc controlled regulation of the gene of interest, the effective intracellular concentration of the transactivator will be primarily a function of the transcriptional activity of a particular locus, a parameter which appears unpredictable and impossible to control. One way to overcome these limitations would be to adapt the activation potential of the transactivator to the expression level of a specific locus.

Here we describe a panel of novel Tc controlled transactivators which contain VP16 derived minimal activation domains and which possess a graded transactivation potential spanning more than 3 orders of magnitude. These transactivators are tolerated in cells at higher concentrations and, therefore, appear suitable for experimental approaches as described above.

The transcriptional transactivators described in the Examples are fusions between the Tet repressor and minimal activation domains derived from a 12 amino acid segment comprising the "acidic activation domain" of VP16. This 12 amino acid segment spans from amino acid positions 436 to 447 of VP16. In certain embodiments of the invention, the transcriptional activator fusion protein contains three or four copies of this region. A fusion protein containing three copies of this region has approximately 100% of the transcriptional activation potential of TetR-VP16 (i.e., TetR fused to about 127 C-terminal amino acids of VP16). A fusion protein containing four copies of this region has approximately 230% of the transcriptional activation potential of TetR-VP16.

Mutational analysis of the acidic activation domains of VP16 has revealed that the phenylalanine at position 442 is important for function (Regier, J. L., et al. (1993) *Proc. Natl. Acad. Sci. USA*. 90, 883–887). When replaced by aromatic amino acids like Tyr or Trp or by hydrophobic amino acids such as Leu, Ile or Ala, the activation potential of a truncated VP16 was reduced approximately 3 and 10 fold, respectively. All other substitutions caused an even larger loss of activity. As described in the Examples, transactivator fusion proteins comprising mutated acidic domains of VP16 provide a panel of fusion proteins with graded transactivation potential. In one embodiment of the invention, the transactivator fusion protein contains at least one copy of amino acid positions 436 to 447, wherein the phenylalanine at position 442 has been mutated. In one embodiment, the phenylalanine at position 442 is changed to glycine. In another embodiment, the phenylalanine at position 442 is changed to tyrosine. In yet other embodiments, the phenylalanine at position 442 is changed to tryptophan, leucine, isoleucine or alanine. Various combinations of wild type and mutant acidic regions are also encompassed by the invention, examples of which include: VP16[G][G] (SEQ ID NO: 4), VP16[F][G] (SEQ ID NO: 5), VP16[G][F] (SEQ ID NO: 6), VP16[F][G][Y] (SEQ ID NO: 7) and VP16[G][F][Y] (SEQ ID NO: 8) (wherein the letter within the bracket indicates the amino acid at position 442 in standard one-letter code).

Combination of several of these minimal domains using wild type as well as mutated sequences yielded a panel of transactivators (tTA1 to tTA7, Table 1) which differ in their activation potential by more than 3 orders of magnitude whereby tTA1 exceeds the activation strength of the previously described tTA 2.3 fold. The new transactivators activate the previously described tTA responsive promoter, $P_{hCMV^*-1}$ (Gossen, M., and Bujard, H. (1992) *Proc. Natl. Acad. Sci. U.S.A.* 89, 5547–5551) despite the fact that a number of sites known to interact with cellular transcription factors were eliminated. Thus, when compared to VP16, tTA1 to tTA7 have lost sites which contact Oct-1 (Hayes, S., and O'Hare, P. (1993) *J. Virol* 67, 852–862) and the host cell factor HCF (Wu, T. J., et al. (1994) *Mol. Cell. Biol.* 14, 3484–3493), both required for formation of the C1 complex comprising Oct-1, HCF, VP16 and DNA (Hayes, S., and O'Hare, P. (1993) *J. Virol* 67, 852–862). Similarly, deletion of the second C-terninal acidic activation domain of VP16 known to contact TAFII40 (Goodrich, J. A., et al. (1993) *Cell* 75, 519–530) and ADA2 (Silverman, N., et al. (1994) *Proc. Natl. Acad. Sci. U.S.A.* 91, 11665–11668) is expected to further reduce the interaction of the new transactivators with those factors. Therefore, we assume that these tTA proteins have gained specificity while their capacity for squelching is reduced. This assumption is supported by the finding that tTA2 is tolerated in HeLa cells at 3-fold higher concentrations than the original TetR-VP16 fusion (tTA) although both transactivators possess the same activation potential (Table 1). It thus appears that elements of VP16 were removed which have limited the expression to a lower level. When the intracellular concentration of tTA2, tTA3 and tTA4 are compared, an inverse correlation with the respective activation potential is revealed. It thus appears feasable to use the panel of transactivators described here for the adjustment of transactivating capacities to expression signals of different strength.

Fusion of acidic domains to DNA binding proteins as described here increases the negative charge of the molecule and thus may affect its affinity to DNA. However, DNA retardation experiments shown herein demonstrate that all TetR fusions bind to tetO sequences with comparable efficiency although minor differences between the various binding constants would not be revealed by this assay.

Fusing a single [F] domain to TetR yielded a protein that does not activate transcription. Fusing a second minimal activation domain to TetR-F resulting in TetR-FF (tTA3) generates a transactivator which reaches approximately 40% of the activity of tTA. Adding further [F]-domains to the tTA3 increased the activation capacity approximately 2.5 fold per domain as seen for tTA2 and tTA1.

Comparing TetR-F with TetR-GF (tTA6) indicates that adding a [G]-domain, which by itself is transcriptionally inactive since TetR-GG is not effective, suffices to generate a functional transactivator, tTA6. The transactivator with the inverse order of the two minimal domains, TetR-FG (TA7), is less active than tTA6 indicating that steric factors contribute to a functional arrangement of activating domains. Since tTA7 has nevertheless a measurable activity we must conclude that the negative charges of the [G]-domain contribute to transcriptional activity as well. tTA6 and tTA7 are all very weak transactivators. By simply exchanging the glycine for a phenylalanine the activation potential of the resulting transactivator (tTA3) is increased approximately 60 fold (tTA6) or even more than 1000 fold (tTA7). From this we conclude that in our system at least two minimal activation modules acting synergistically are required for efficient stimulation of transcription. The activation properties of tTA5 and tTA4 may again be explained by steric and synergistic effects exerted by the combination of the respective minimal domains, whereby the addition of the [Y]-domain to both, tTA6 and tTA7, increases the activation potential 20 fold.

The panel of Tc controlled transactivators described here offers a number of advantages. First, it allows to adapt the capacity of a transactivator to the strength of a given promoter. This opens up new possibilities for achieving cell type-restricted Tc controlled regulation in transgenic organisms by placing a tTA coding sequence under control of a cellular promoter via homologous recombination. Since neither the strength of the targeted promoter nor the intracellular tTA concentration originating from such a locus can be readily predicted, choice of transactivators differing in strength will yield an additional degree of freedom for finding the appropriate promoter/transactivator combination. Second, due to their increased specificity and their reduced squelching capacity, the new tTAs should facilitate the generation of cell lines and transgenic animals constitutively producing tTA in proper amounts. Third, by reducing the size of the activation domain of the original tTA numerous sequence motifs potentially capable of eliciting a cellular immune response were eliminated. Therefore, the transactivators characterized here may be preferred whenever interference with the cellular immune response is expected although such a response has not been observed for tTA/rtTA in the mouse model so far. Finally, the small size of the new transactivators may be of advantage when integration into vector systems with limited capacity for foreign sequences is considered.

Additional aspects of the invention are described in further detail in the following subsections.

I. Transcriptional Activator Fusion Proteins

One aspect of the invention pertains to fusion proteins and nucleic acids (e.g., DNA) encoding fusion proteins. The term "fusion protein" is intended to describe at least two polypeptides, typically from different sources, which are operatively linked. With regard to the polypeptides, the term "operatively linked" is intended to mean that the two polypeptides are connected in manner such that each polypeptide can serve its intended function. Typically, the two polypeptides are covalently attached through peptide bonds. The fusion protein is preferably produced by standard recombinant DNA techniques. For example, a DNA molecule encoding the first polypeptide is ligated to another DNA molecule encoding the second polypeptide, and the resultant hybrid DNA molecule is expressed in a host cell to produce the fusion protein. The DNA molecules are ligated to each other in a 5' to 3' orientation such that, after ligation, the translational frame of the encoded polypeptides is not altered (i.e., the DNA molecules are ligated to each other in-frame).

The transactivator fusion protein of the invention is composed, in part, of a first polypeptide which binds to DNA (i.e., the first polypeptide comprises a DNA binding domain.). Preferred DNA binding domains include the Tet repressor and a mutated Tet repressor that binds to tet operator sequences in the presence, but not the absence, of tetracycline (Tc), or an analogue thereof. Compositions and methods for creating fusions of TetR to VP16 (to create tTA) and mutated TetR to VP16 (to create rtTA) are described in U.S. Pat. No. 5,464,758, U.S. Pat. No. 5,589,362, PCT Publication WO 94/29442, PCT Publication, WO 96/01313 and PCT Publication WO 96/40892. These compositions and methods can be applied to create the fusions of the invention using standard molecular biology techniques and the guidance provided in the exemplification. Other suitable DNA binding domains include GAL4, LexA, LacR and hormone receptors, which also can be fused to the VP16-derived minimal activation domains of the invention using standard recombinant DNA techniques.

The first polypeptide of the transactivator fusion protein is operatively linked to a second polypeptide derived from the minimal activation domain of VP16. To operatively link the first and second polypeptides, typically nucleotide sequences encoding the first and second polypeptides are ligated to each other in-frame to create a chimeric gene encoding a fusion protein, although the first and second polypeptides can be operatively linked by other means that preserve the function of each polypeptide (e.g., chemically crosslinked). Further details of the VP16-derived minimal activation domains of the invention are provided in the Examples.

II. Expression of a Transactivator Fusion Protein

A. Expression Vectors

A nucleic acid of the invention encoding a transactivator fusion protein, as described above, can be incorporated into a recombinant expression vector in a form suitable for expression of the fusion protein in a host cell. The term "in a form suitable for expression of the fusion protein in a host cell" is intended to mean that the recombinant expression vector includes one or more regulatory sequences operatively linked to the nucleic acid encoding the fusion protein in a manner which allows for transcription of the nucleic acid into mRNA and translation of the mRNA into the fusion protein. The term "regulatory sequence" is art-recognized and intended to include promoters, enhancers and other expression control elements (e.g., polyadenylation signals). Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the amount of fusion protein to be expressed.

When used in mammalian cells, a recombinant expression vector's control functions are often provided by viral genetic material. For example, commonly used promoters are derived from polyoma, Adenovirus 2, cytomegalovirus and Simian Virus 40. Use of viral regulatory elements to direct expression of the fusion protein can allow for high level constitutive expression of the fusion protein in a variety of host cells. In a preferred recombinant expression vector, the sequences encoding the fusion protein are flanked upstream (i.e., 5') by the human cytomegalovirus IE promoter and downstream (i.e., 3') by an SV40 poly(A) signal. For example, an expression vector similar to that described in Example 1 can be used. The human cytomegalovirus IE promoter is described in Boshart et al. (1985) *Cell* 41:521–530. Other ubiquitously expressing promoters which can be used include the HSV-Tk promoter (disclosed in McKnight et al. (1984) *Cell* 37:253–262) and β-actin promoters (e.g., the human β-actin promoter as described by Ng et al. (1985) *Mol. Cell. Biol.* 5:2720–2732).

Alternatively, the regulatory sequences of the recombinant expression vector can direct expression of the fusion protein preferentially in a particular cell type, i.e., tissue-specific regulatory elements can be used. Non-limiting examples of tissue-specific promoters which can be used include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Alternatively, a self-regulating construct encoding a transactivator fusion protein can be created. To accomplish this, nucleic acid encoding the fusion protein is operatively linked to a regulatory sequences that include the DNA binding site to which the DNA binding domain of the fusion protein binds. For example, for the tet system, tTA- or rtTA-coding sequences can be operatively linked to a minimal promoter sequence and at least one tet operator sequence.

In one embodiment, the recombinant expression vector of the invention is a plasmid. Alternatively, a recombinant expression vector of the invention can be a virus, or portion thereof, which allows for expression of a nucleic acid introduced into the viral nucleic acid. For example, replication defective retroviruses, adenoviruses and adeno-associated viruses can be used. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. The genome of adenovirus can be manipulated such that it encodes and expresses a transactivator fusion protein but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Alternatively, an adeno-associated virus vector such as that described in Tratschin et al. (1985) *Mol. Cell. Biol.* 5:3251–3260 can be used to express a transactivator fusion protein.

B. Host Cells

A fusion protein of the invention is expressed in a eukaryotic cell by introducing nucleic acid encoding the fusion protein into a host cell, wherein the nucleic acid is in a form suitable for expression of the fusion protein in the host cell. For example, a recombinant expression vector of the invention, encoding the fusion protein, is introduced into a host cell. Alternatively, nucleic acid encoding the fusion protein which is operatively linked to regulatory sequences (e.g., promoter sequences) but without additional vector sequences can be introduced into a host cell. As used herein, the term "host cell" is intended to include any eukaryotic cell or cell line so long as the cell or cell line is not incompatible with the protein to be expressed, the selection system chosen or the fermentation system employed. Non-limiting examples of mammalian cell lines which can be used include CHO dhfr⁻ cells (Urlaub and Chasin (1980) *Proc. Natl. Acad. Sci. USA* 77:4216–4220), 293 cells (Graham et al. (1977) *J. Gen. Virol.* 36: pp59) or myeloma cells like SP2 or NS0 (Galfre and Milstein (1981) *Meth. Enzymol.* 73(B) :3–46).

In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, neuronal cells and skin epithelium and airway epithelium. Additionally, for transgenic or homologous recombinant animals, embryonic stem cells and fertilized oocytes can be modified to contain nucleic acid encoding a transactivator fusion protein. Moreover, plant cells can be modified to create transgenic plants.

The invention is broadly applicable and encompasses non-mammalian eukaryotic cells as well, including insect (e.g., Sp. frugiperda), yeast (e.g., *S. cerevisiae, S. pombe, P. pastoris, K. lactis, H. polymorpha*; as generally reviewed by Fleer, R. (1992) *Current Opinion in Biotechnology* 3(5) :486–496)), fungal and plant cells. Examples of vectors for expression in yeast *S. cerivisae* include pYepSec1 (Baldari. et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). The fusion protein can be expressed in insect cells using baculovirus expression vectors (e.g., as described in O'Reilly et al. (1992) *Baculovirus Expression Vectors: A Laboratory Manual*, Stockton Press). Baculovirus vectors available for expression of proteins in cultured insect cells (e.g., SF 9 cells) include the pAc series (Smith et al., (1983) *Mol. Cell Biol.* 3:2156–2165) and the pVL series (Lucklow, V. A., and Summers, M. D., (1989) *Virology* 170:31–39).

C. Introduction of Nucleic Acid into a Host Cell

Nucleic acid encoding the fusion protein can be introduced into a host cell by standard techniques for transfecting eukaryotic cells. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (*Molecular Cloning: A Laboratory Manual*, 2nd Edition, Cold Spring Harbor Laboratory press (1989)), and other laboratory textbooks.

The number of host cells transformed with a nucleic acid of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

A host cell transfected with a nucleic acid encoding a fusion protein of the invention can be further transfected with one or more nucleic acids which serve as the target for the fusion protein. For example, for the tet system, the target nucleic acid comprises a nucleotide sequence to be transcribed operatively linked to at least one tet operator sequence.

Nucleic acid encoding the fusion protein of the invention can be introduced into eukaryotic cells growing in culture in vitro by conventional transfection techniques (e.g., calcium phosphate precipitation, DEAE-dextran transfection, electroporation etc.). Nucleic acid can also be transferred into cells in vivo, for example by application of a delivery mechanism suitable for introduction of nucleic acid into cells in vivo, such as retroviral vectors (see e.g., Ferry, N et al. (1991) *Proc. Natl. Acad. Sci. USA* 88:8377–8381; and Kay, M. A. et al. (1992) *Human Gene Therapy* 3:641–647), adenoviral vectors (see e.g., Rosenfeld, M. A. (1992) *Cell* 68:143–155; and Herz, J. and Gerard, R. D. (1993) *Proc. Natl. Acad. Sci. USA* 90:2812–2816), receptor-mediated DNA uptake (see e.g., Wu, G. and Wu, C. H. (1988) *J. Biol. Chem.* 263:14621; Wilson et al. (1992) *J. Biol. Chem.* 267:963–967; and U.S. Pat. No. 5,166,320), direct injection of DNA (see e.g., Acsadi et al. (1991) *Nature* 332: 815–818; and Wolff et al. (1990) *Science* 247:1465–1468) or particle bombardment (see e.g., Cheng, L. et al. (1993) *Proc. Natl. Acad. Sci. USA* 90:4455–4459; and Zelenin, A. V. et al. (1993) *FEBS Letters* 315:29–32). Thus, for gene therapy purposes, cells can be modified in vitro and administered to a subject or, alternatively, cells can be directly modified in vivo.

D. Transgenic Organisms

Nucleic acid a transactivator fusion protein can transferred into a fertilized oocyte of a non-human animal to create a transgenic animal which expresses the fusion protein of the invention in one or more cell types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. In one embodiment, the non-human animal is a mouse, although the invention is not limited thereto. In other embodiments, the transgenic animal is a goat, sheep, pig, cow or other domestic farm animal. Such transgenic animals are useful for large scale production of proteins (so called "gene pharming").

A transgenic animal can be created, for example, by introducing a nucleic acid encoding the fusion protein (typically linked to appropriate regulatory elements, such as a constitutive or tissue-specific enhancer) into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) *A Laboratory Manual*, Cold Spring Harbor, N.Y., Cold Spring Harbor Laboratory. A transgenic founder animal can be used to breed additional animals carrying the transgene. Transgenic animals carrying a transgene encoding the fusion protein of the invention can further be bred to other transgenic animals carrying a transgene comprising a gene of interest operatively linked to the target DNA site to which the transactivator fusion protein binds. For example, for the tet system, a tTA- or rtTA-transgenic animal can be bred to a transgenic animal which contains a gene operatively linked to a tet operator sequence.

It will be appreciated that, in addition to transgenic animals, the regulatory system described herein can be applied to other transgenic organisms, such as transgenic plants. Transgenic plants can be made by conventional techniques known in the art. Accordingly, the invention encompasses non-human transgenic organisms, including animals and plants, that contains cells which express the transactivator fusion protein of the invention (i.e., a nucleic acid encoding the transactivator is incorporated into one or more chromosomes in cells of the transgenic organism).

E. Homologous Recombinant Organisms

The invention also provides a homologous recombinant non-human organism expressing the fusion protein of the invention. The term "homologous recombinant organism" as used herein is intended to describe an organism, e.g. animal or plant, containing a gene which has been modified by homologous recombination between the gene and a DNA molecule introduced into a cell of the animal, e.g., an embryonic cell of the animal. In one embodiment, the non-human animal is a mouse, although the invention is not limited thereto. An animal can be created in which nucleic acid encoding the fusion protein has been introduced into a specific site of the genome, i.e., the nucleic acid has homologously recombined with an endogenous gene.

To create such a homologous recombinant animal, a vector is prepared which contains DNA encoding the fusion protein flanked at its 5' and 3' ends by additional nucleic acid of a eukaryotic gene at which homologous recombination is to occur. The additional nucleic acid flanking that encoding the fusion protein is of sufficient length for successful homologous recombination with the eukaryotic gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA. These "germline transmission" animals can further be mated to animals carrying a gene operatively linked to a target DNA site to which the transactivator fusion protein binds. For example, for the tet system, the germline transmission" animals can further be mated to animals carrying a gene operatively linked to at least one tet operator sequence.

In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res.* 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet.* 13:367–375; and Fiering, S. et al. (1993) *Proc. Natl. Acad. Sci. USA* 90:8469–8473).

III. Kits of the Invention

Another aspect of the invention pertains to kits which include the components of the regulatory system of the invention. Such a kit can be used to regulate the expression of a gene of interest (i.e., a nucleotide sequence of interest to be transcribed). The kit may include nucleic acid encoding a transcriptional activator fusion protein.

Alternatively, eukaryotic cells which have nucleic acid encoding a transactivator fusion protein stably incorporated therein, such that the transactivator fusion protein is expressed in the eukaryotic cell, may be provided in the kit.

In one embodiment, the kit includes a carrier means having in close confinement therein at least two container means: a first container means which contains a first nucleic acid (e.g., DNA) encoding a transactivator fusion protein of the invention, and a second container means which contains a second target nucleic acid (e.g., DNA) for the transactivator into which a nucleotide sequence of interest can be cloned. The second nucleic acid typically comprises a cloning site for introduction of a nucleotide sequence to be transcribed (optionally including an operatively linked minimal promoter sequence) and at least one operatively linked DNA binding site to which the fusion protein binds. The term "cloning site" is intended to encompass at least one restriction endonuclease site. Typically, multiple different restriction endonuclease sites (e.g., a polylinker) are contained within the nucleic acid.

To regulate expression of a nucleotide sequence of interest using the components of the kit, the nucleotide sequence of interest is cloned into the cloning site of the target vector of the kit by conventional recombinant DNA techniques and then the first and second nucleic acids are introduced into a host cell or animal. The transactivator fusion protein expressed in the host cell or animal then regulates transcription of the nucleotide sequence of interest (either constitutively or in the presence or absence of an appropriate inducing agent, depending on which DNA binding domain in used in the fusion protein).

Alternatively, in another embodiment, the kit includes a eukaryotic cell which is stably transfected with a nucleic acid encoding a transactivator fusion protein of the invention such that the transactivator is expressed in the cell. Thus, rather than containing nucleic acid alone, the first container means described above can contain a eukaryotic cell line into which the first nucleic acid encoding the transactivator has been stably introduced (e.g., by stable transfection by a conventional method such as calcium phosphate precipitation or electroporation, etc.). In this embodiment, a nucleotide sequence of interest is cloned into the cloning site of the target vector of the kit and then the target vector is introduced into the eukaryotic cell expressing the transactivator fusion protein.

IV. Regulation of Gene Expression by Tetracycline or Analogues Thereof

In a host cell which carries nucleic acid encoding a transactivator fusion protein of the invention based on the tet system or the reverse tet system, as well as a nucleotide sequence operatively linked to the tet operator sequence(i.e., gene of interest to be transcribed), high level transcription of the nucleotide sequence operatively linked to the tet operator sequence(s) is dependent upon the presence or absence of tetracycline (depending upon whether the tet or reverse tet system is used). In order to induce transcription in a host cell, the host cell is either cultured in the absence of Tc (for the tet system) or contacted with tetracycline or a tetracycline analogue (for the reverse tet system). Accordingly, another aspect of the invention pertains to methods for regulating transcription of a nucleotide sequence operatively linked to a tet operator sequence in a host cell or animal which expresses a transactivator fusion protein of the invention. The methods involve contacting the cell with tetracycline or a tetracycline analogue or administering tetracycline or a tetracycline analogue to a subject containing the cell.

The term "tetracycline analogue" is intended to include compounds which are structurally related to tetracycline and which bind to the Tet repressor with a $K_a$ of at least about $10^6$ $M^{-1}$. Preferably, the tetracycline analogue binds with an affinity of about $10^9$ $M^{-1}$ or greater. Examples of such tetracycline analogues include, but are not limited to, anhydrotetracycline, doxycycline, chlorotetracycline, oxytetracycline and others disclosed by Hlavka and Boothe, "The Tetracyclines," in *Handbook of Experimental Pharmacology* 78, R. K. Blackwood et al. (eds.), Springer-Verlag, Berlin-N.Y., 1985; L. A. Mitscher, "The Chemistry of the Tetracycline Antibiotics", *Medicinal Research* 9, Dekker, New York, 1978; Noyee Development Corporation, "Tetracycline Manufacturing Processes" *Chemical Process Reviews*, Park Ridge, N.J., 2 volumes, 1969; R. C. Evans, "The Technology of the Tetracyclines", *Biochemical Reference Series* 1, Quadrangle Press, New York, 1968; and H. F. Dowling, "Tetracycline", *Antibiotic Monographs*, no. 3, Medical Encyclopedia, New York, 1955. Preferred Tc analogues for high level stimulation of transcription are anhydrotetracycline and doxycycline. A Tc analogue can be chosen which has reduced antibiotic activity compared to Tc. Examples of such Tc analogues are anhydrotetracycline, epioxytetracycline and cyanotetracycline.

To modulate gene expression in a cell in vitro, the cell is contacted with Tc or a Tc analogue by culturing the cell in a medium containing the compound. When culturing cells in vitro in the presence of Tc or Tc analogue, a preferred concentration range is between about 10 and about 1000 ng/ml. Tc or a Tc analogue can be directly added to media in which cells are already being cultured, or more preferably for high levels of gene induction, cells are harvested from Tc-free media and cultured in fresh media containing Tc, or an analogue thereof.

To induce gene expression in vivo, cells within in a subject are contacted with Tc or a Tc analogue by administering the compound to the subject. The term "subject" is intended to include humans and other non-human mammals including monkeys, cows, goats, sheep, dogs, cats, rabbits, rats, mice, and transgenic and homologous recombinant species thereof Furthermore, the term "subject" is intended to include plants, such as transgenic plants. When the inducing agent is administered to a human or animal subject, the dosage is adjusted to preferably achieve a serum concentration between about 0.05 and 1.0 1 µg/ml. Tc or a Tc analogue can be administered to a subject by any means effective for achieving an in vivo concentration sufficient for gene induction. Examples of suitable modes of administration include oral administration (e.g., dissolving the inducing agent in the drinking water), slow release pellets and implantation of a diffusion pump. To administer Tc or a Tc analogue to a transgenic plant, the inducing agent can be dissolved in water administered to the plant.

VI. Applications of the Invention

The invention is widely applicable to a variety of situations where it is desirable to be able to turn gene expression on and off, or regulate the level of gene expression, in a rapid, efficient and controlled manner without causing pleiotropic effects or cytotoxicity. Thus, the system of the invention has widespread applicability to the study of cellular development and differentiation in eukaryotic cells, plants and animals. For example, expression of oncogenes can be regulated in a controlled manner in cells to study their function. Additionally, the system can be used to regulate the expression of site-specific recombinases, such as CRE or FLP, to thereby allow for irreversible modification of the genotype of a transgenic organism under controlled conditions at a particular stage of development. For example, drug resistance markers inserted into the genome of transgenic plants that allow for selection of a particular transgenic plant could be irreversibly removed via a Tc-regulated site specific recombinase. Other applications of the regulatory system of the invention include:

A. Gene Therapy

The invention may be particularly useful for gene therapy purposes, in treatments for either genetic or acquired diseases. The general approach of gene therapy involves the introduction of nucleic acid into cells such that one or more gene products encoded by the introduced genetic material are produced in the cells to restore or enhance a functional activity. For reviews on gene therapy approaches see Anderson, W. F. (1992) *Science* 256:808–813; Miller, A. D. (1992) *Nature* 357:455–460; Friedmann, T. (1989) *Science* 244:1275–1281; and Cournoyer, D., et al. (1990) *Curr. Opin. Biotech.* 1:196–208. However, current gene therapy vectors typically utilize constitutive regulatory elements which are responsive to endogenous transcriptions factors. These vector systems do not allow for the ability to modulate the level of gene expression in a subject. In contrast, the inducible regulatory system of the invention provides this ability.

To use the reverse tet system of the invention for gene therapy purposes, in one embodiment, cells of a subject in need of gene therapy are modified to contain 1) nucleic acid encoding a transactivator fusion protein of the invention in a form suitable for expression of the transactivator in the host cells and 2) a gene of interest (e.g., for therapeutic purposes) operatively linked to a tet operator sequence(s). The cells of the subject can be modified ex vivo and then introduced into the subject or the cells can be directly modified in vivo. Expression of the gene of interest in the cells of the subject is then stimulated by administering Tc or a Tc analogue to the patient. The level of gene expression can be varied depending upon which particular Tc analogue is used as the inducing agent. The level of gene expression can also be modulated by adjusting the dose of the tetracycline, or analogue thereof, administered to the patient to thereby adjust the concentration achieved in the circulation and the tissues of interest.

Conventional detection methods known in the art, such as an enzyme linked immunosorbent assay, can be used to monitor the expression of the regulated protein of interest in the host cells and the concentration of Tc or Tc analogue can be varied until the desired level of expression of the protein of interest is achieved. Accordingly, expression of a protein of interest can be adjusted according to the medical needs of an individual, which may vary throughout the lifetime of the individual. To stop expression of the gene of interest in cells of the subject, administration of the inducing agent is stopped. Thus, the regulatory system of the invention offers the advantage over constitutive regulatory systems of allowing for modulation of the level of gene expression depending upon the requirements of the therapeutic situation.

Genes of particular interest to be expressed in cells of a subject for treatment of genetic or acquired diseases include those encoding adenosine deaminase, Factor VIII, Factor IX, dystrophin, β-globin, LDL receptor, CFTR, insulin, erythropoietin, anti-angiogenesis factors, growth hormone, glucocerebrosidase, β-glucouronidase, α1-antitrypsin, phenylalanine hydroxylase, tyrosine hydroxylase, omithine transcarbamylase, arginosuccinate synthetase, UDP-glucuronysyl transferase, apoA1, TNF, soluble TNF receptor, interleukins (e.g., IL-2), interferons (e.g., α- or γ-IFN) and other cytokines and growth factors. Cells types which can be modified for gene therapy purposes include hematopoietic stem cells, myoblasts, hepatocytes, lymphocytes, skin epithelium and airway epithelium. For further descriptions of cell types, genes and methods for gene therapy see e.g., Wilson, J. M et al. (1988) *Proc. Natl. Acad. Sci. USA* 85:3014–3018; Armentano, D. et al. (1990) *Proc. Natl. Acad. Sci. USA* 87:6141–6145; Wolff, J. A. et al. (1990) *Science* 247:1465–1468; Chowdhury, J. R. et al. (1991) *Science* 254:1802–1805; Ferry, N. et al. (1991) *Proc. Natl. Acad. Sci. USA* 88:8377–8381; Wilson, J. M. et al. (1992) *J. Biol. Chem.* 267:963–967; Quantin, B. et al. (1992) *Proc. Natl. Acad. Sci. USA* 89:2581–2584; Dai, Y. et al. (1992) *Proc. Natl. Acad. Sci. USA* 89:10892–10895; van Beusechem, V. W. et al. (1992) *Proc. Natl. Acad. Sci. USA* 89:7640–7644; Rosenfeld, M. A. et al. (1992) *Cell* 68:143–155; Kay, M. A. et al. (1992) *Human Gene Therapy* 3:641–647; Cristiano, R. J. et al. (1993) *Proc. Natl. Acad. Sci. USA* 90:2122–2126; Hwu, P. et al. (1993) *J. Immunol.* 150:4104–4115; and Herz, J. and Gerard, R. D. (1993) *Proc. Natl. Acad. Sci. USA* 90:2812–2816.

Gene therapy applications of particular interest in cancer treatment include overexpression of a cytokine gene (e.g., TNF-α) in tumor infiltrating lymphocytes or ectopic expression of cytokines in tumor cells to induce an anti-tumor immune response at the tumor site), expression of an enzyme in tumor cells which can convert a non-toxic agent into a toxic agent, expression of tumor specific antigens to induce an anti-tumor immune response, expression of tumor suppressor genes (e.g., p53 or Rb) in tumor cells, expression of a multidrug resistance gene (e.g., MDR1 and/or MRP) in bone marrow cells to protect them from the toxicity of chemotherapy.

Gene therapy applications of particular interest in treatment of viral diseases include expression of trans-dominant negative viral transactivation proteins, such as trans-dominant negative tat and rev mutants for HIV or trans-dominant ICp4 mutants for HSV (see e.g., Balboni, P. G. et al. (1993) *J. Med. Virol.* 41:289–295; Liem, S. E. et al. (1993) *Hum. Gene Ther.* 4:625–634; Malim, M. H. et al. (1992) *J. Exp. Med.* 176:1197–1201; Daly, T. J. et al. (1993) *Biochemistry* 32:8945–8954; and Smith, C. A. et al. (1992) *Virology* 191:581–588), expression of trans-dominant negative envelope proteins, such as env mutants for HIV (see e.g., Steffy, K. R. et al. (1993) *J. Virol.* 67:1854–1859), intracellular expression of antibodies, or fragments thereof, directed to viral products ("internal immunization", see e.g., Marasco, W. A. et al. (1993) *Proc. Natl. Acad. Sci. USA* 90:7889–7893) and expression of soluble viral receptors, such as soluble CD4. Additionally, the system of the invention can be used to conditionally express a suicide gene in cells, thereby allowing for elimination of the cells after they have served an intended function. For example, cells used for vaccination can be eliminated in a subject after an immune response has been generated the subject by inducing expression of a suicide gene in the cells by administering Tc or a Tc analogue to the subject.

The Tc-controlled regulatory system of the invention has numerous advantages properties that it particularly suitable for application to gene therapy. For example, the system provides an "on"/"off" switch for gene expression that allows for regulated dosaging a gene product in a subject. There are several situations in which it may be desirable to be able to provide a gene product at specific levels and/or times in a regulated manner, rather than simply expressing the gene product constitutively at a set level. For example, a gene of interest can be switched "on" at fixed intervals (e.g., daily, alternate days, weekly, etc.) to provide the most effective level of a gene product of interest at the most effective time. The level of gene product produced in a subject can be monitored by standard methods (e.g., direct monitoring using an immunological assay such as ELISA or RIA or indirectly by monitoring of a laboratory parameter dependent upon the function of the gene product of interest, e.g., blood glucose levels and the like). This ability to turn "on" expression of a gene at discrete time intervals in a subject while also allowing for the gene to be kept "off" at other times avoids the need for continued administration of a gene product of interest at intermittent intervals. This approach avoids the need for repeated injections of a gene product, which may be painful and/or cause side effects and would likely require continuous visits to a physician. In contrast, the system of the invention avoids these drawbacks. Moreover, the ability to turn "on" expression of a gene at discrete time intervals in a subject allows for focused treatment of diseases which involve "flare ups" of activity (e.g., many autoimmune diseases) only at times when treatment is necessary during the acute phase when pain and symptoms are evident. At times when such diseases are in remission, the expression system can be kept in the "off" state.

Gene therapy applications that may particularly benefit from this ability to modulate gene expression during discrete time intervals include the following non-limiting examples:

Rheumatoid arthritis—genes which encode gene products that inhibit the production of inflammatory cytokines (e.g., TNF, IL-1 and IL-12). can be expressed in subjects. Examples of such inhibitors include soluble forms of a receptor for the cytokine. Additionally or alternatively, the cytokines IL-10 and/or IL-4 (which stimulate a protective Th2-type response) can be expressed. Moreover, a glucocorticomimetic receptor (GCMR) can be expressed.

Hypopituitarism—the gene for human growth hormone can be expressed in such subjects only in early childhood, when gene expression is necessary, until normal stature is achieved, at which time gene expression can be downregulated.

Wound healing/Tissue regeneration—Factors (e.g., growth factors, angiogenic factors, etc.) necessary for the healing process can be expressed only when needed and then downregulated.

Anti-Cancer Treatments—Expression of gene products useful in anti-cancer treatment can be limited to a therapeutic phase until retardation of tumor growth is achieved, at which time expression of the gene product can be downregulated. Possible systemic anti-cancer treatments include use of tumor infiltrating lymphocytes which express immunostimulatory molecules (e.g., IL-2, IL-12 and the like), angiogenesis inhibitors (PF4, IL-12, etc.), Her-regulin, Leukoregulin (see PCT Publication No. WO 85/04662), and growth factors for bone marrow support therapy, such as G-CSF, GM-CSF and M-CSF. Regarding the latter, use of the regulatory system of the invention to express factors for bone marrow support therapy allows for simplified therapeutic switching at regular intervals from chemotherapy to bone marrow support therapy (similarly, such an approach can also be applied to AIDS treatment, e.g., simplified switching from anti-viral treatments to bone marrow support treatment). Furthermore, controlled local targeting of anti-cancer treatments are also possible. For example, expression of a suicide gene by a regulator of the invention, wherein the regulator itself is controlled by, for example, a tumor-specific promoter or a radiation-induced promoter.

In another embodiment, the regulatory system of the invention is used to express angiogenesis inhibitor(s) from within a tumor via a transgene regulated by the system of the invention. Expression of angiogenesis inhibitors in this manner may be more efficient than systemic administration of the inhibitor and would avoid any deleterious side effects that might accompany systemic administration. In particular, restricting angiogenesis inhibitor expression to within tumors could be particularly useful in treating cancer in children still undergoing angiogenesis associated with normal cell growth.

In another embodiment, high level regulated expression of cytokines may represent a method for focusing a patients own immune response on tumor cells. Tumor cells can be transduced to express chemoattractant and growth promoting cytokines important in increasing an individual's natural immune response. Because the highest concentrations of cytokines will be in the proximity of the tumor, the likelihood of eliciting an immunological response to tumor antigens is increased. A potential problem with this type of therapy is that those tumor cells producing the cytokines will also be targets of the immune response and therefor the source of the cytokines will be eliminated before eradication of all tumor cells can be certain. To combat tls, expression of viral proteins known to mask infected cells from the immune system can be placed under regulation, along with the cytokine gene(s), in the same cells. One such protein is the E19 protein from adenovirus (see e.g., Cox, *Science* 247:715). This protein prevents transport of class I HLA antigens to the surface of the cell and hence prevents recognition and lysis of the cell by the host's cytotoxic T cells. Accordingly, regulated expression of E19 in tumor cells could shield cytokine producer cells from cytotoxic T cells during the onset of an immune response provoked by cytokine expression. After a sufficient period of time has elapsed to eradicate all tumor cells but those expressing E19, E19 expression can be turned off, causing these cells then to fall victim to the provoked anti-tumor immune response.

Benign prostatic hypertrophy—Similar to the above, a suicide gene can be regulated by a regulator of the invention, wherein the regulator itself is controlled by, for example, a prostate-specific promoter.

The ability to express a suicide gene (e.g., an apoptosis gene, TK gene, etc) in a controlled manner using the regulatory system of the invention adds to the general safety and usefulness of the system. For example, at the end of a desired therapy, expression of a suicide gene can be triggered to eliminate cells carrying the gene therapy vector, such as cells in a bioinert implant, cells that have disseminated beyond the intended original location, etc. Moreover, if a transplant becomes tumorous or has side effects, the cells can be rapidly eliminated by induction of the suicide gene. The use of more than one Tc-controlled "on"/"off" switch in one cell allows for completely independent regulation of a suicide gene compared to regulation of a gene of therapeutic interest (as described in detail herein).

The regulatory system of the invention further offers the ability to establish a therapeutically relevant expression level for a gene product of interest in a subject, in contrast to unregulated constitutive expression which offers no flexibility in the level of gene product expression that can be achieved. A physiologically relevant level of gene product expression can be established based on the particular medical need of the subject, e.g., based on laboratory tests that monitor relevant gene product levels (using methods as described above). In addition to the clinical examples and gene products already discussed above with gene to dosaging of the gene product, other therapeutically relevant gene products which can be expressed at a desired level at a desired time include: Factor XIII and IX in hemophiliacs (e.g., expression can be elevated during times of risk of injury, such as during sports); insulin or amylin in diabetics (as needed, depending on the state of disease in the subject, diet, etc.); erythropoietin to treat erythrocytopenia (as needed, e.g., at end-stage renal failure); low-density lipoprotein receptor (LDLr) or very low-density lipoprotein receptor (VLDLr) for artherosclerosis or gene therapy in liver (e.g, using ex vivo implants). Applications to treatment of central nervous system disorders are also encompassed. For example, in Alzheimer's disease, "fine tuned" expression of choline acetyl transferase (ChAT) to restore acetylcholine levels, neurotrophic factors (e.g., NGF, BDNGF and the like) and/or complement inhibitors (e.g., sCR1, sMCP, sDAF, sCD59 etc.) can be accomplished. Such gene products can be provided, for example, by transplanted cells expressing the gene products in a regulated manner using the system of the invention. Moreover, Parkinson's disease can be treated by "fine tuned" expression of tyrosine hydroxylase (TH) to increase levodopa and dopamine levels.

In addition to the proteinaceous gene products discussed above, gene products that are functional RNA molecules (such as anti-sense RNAs and ribozymes) can be expressed in a controlled manner in a subject for therapeutic purposes. For example, a ribozyme can be designed which discriminates between a mutated form of a gene and a wild-type gene. Accordingly, a "correct" gene (e.g., a wild-type p53 gene) can be introduced into a cell in parallel with introduction of a regulated ribozyme specific for the mutated form of the gene (e.g., a mutated endogenous p53 gene) to remove the defective mRNA expressed from the endogenous gene. This approach is particularly advantageous in situations in which a gene product from the defective gene would interfere with the action of the exogenous wild-type gene.

Expression of a gene product in a subject using the regulatory system of the invention is modulated using tetracycline or analogues thereof. Such drugs can be administered by any route appropriate for delivery of the drug to its desired site of action (e.g., delivery to cells containing a gene whose expression is to be regulated). Depending on the particular cell types involved, preferred routes of administration may include oral administration, intravenous administration and topical administration (e.g., using a transdermal patch to reach cells of a localized transplant under the skin, such as keratinocytes, while avoiding any possible side effects from systemic treatment).

In certain gene therapy situations, it may be necessary or desirable to take steps to avoid or inhibit unwanted immune reactions in a subject receiving treatment. To avoid a reaction against the cells expressing the therapeutic gene product, a subject's own cells are generally used, when possible, to express the therapeutic gene product, either by in vivo modification of the subject's cells or by obtaining cells from the subject, modifying them ex vivo and returning them to the subject. In situations where allogeneic or xenogeneic cells are used to express a gene product of interest, the regulatory system of the invention, in addition to regulating a therapeutic gene, can also be used to regulate one or more genes involved in the immune recognition of the cells to inhibit an immune reaction against the foreign cells. For example, cell-surface molecules involved in recognition of a foreign cell by T lymphocytes can be downmodulated on the surface of a foreign cell used for delivery of a therapeutic gene product, such as by regulated expression in the foreign cell of a ribozyme which cleaves the mRNA encoding the cell-surface molecule. Particularly preferred cell surface molecules which can be downrodulated in this manner to inhibit an unwanted immune response include class I and/or class II major histocompatibility complex (MHC) molecules, costimulatory molecules (e.g., B7-1 and/or B7-2), CD40, and various "adhesion" molecules, such as ICAM-1 or ICAM-2. Using approaches described herein for independent but coordinate regulation of multiple genes in the same cell, the down-regulation of expression of a cell-surface molecule(s) in a host cell can be coordinated with the up-regulation of expression of a therapeutic gene. Accordingly, after therapy is completed and expression of the therapeutic gene is halted, expression of the endogenous cell surface molecule(s) can be restored to normal. Furthermore, as described above regarding anti-cancer treatments, a viral protein (e.g., adenovirus E19 protein) that downmodulates expression of MHC antigens can be regulated in host cells using the system of the invention as a means of avoiding unwanted immunological reactions.

In addition to the foregoing, all conventional methods for generally or specifically downmodulating immune responses in subjects can be combined with the use of the regulatory system of the invention in situations where inhibition of immune responses is desired. General immunosuppressive agents, such as cyclosporin A and/or FK506, can be administered to the subject. Alternatively, immunomodulatory agents which may allow for more specific immunosuppression can be used. Such agents may include inhibitors of costimulatory molecules (e.g., a CTLA4Ig fusion protein, soluble CD4, anti-CD4 antibodies, anti-B7-1 and/or anti-B7-2 antibodies or anti-gp39 antibodies).

Finally, in certain situations, a delivery vehicle for cells expressing a therapeutic gene can be chosen which minimizes exposure of transplanted cells to the immune system. For example, cells can be implanted into bioinert capsules/biocompatible membranes with pores which allow for diffusion of proteins (e.g., a therapeutic gene product of interest) out of the implant and diffusion of nutrients and oxygen into the implant but which prevent entry of immune cells, thereby avoiding exposure of the transplanted cells to the immune system (as has been applied to islet cell transplantation).

B. Production of Proteins in Vitro

Large scale production of a protein of interest can be accomplished using cultured cells in vitro which have been modified to contain 1) a nucleic acid encoding a transactivator fusion protein of the invention in a form suitable for expression of the transactivator in the cells and 2) a gene encoding the protein of interest operatively linked to a tet operator sequence(s). For example, mammalian, yeast or fungal cells can be modified to contain these nucleic acid components as described herein. The modified mammalian, yeast or fungal cells can then be cultured by standard fermentation techniques in the presence of Tc or an analogue thereof to induce expression of the gene and produce the protein of interest. Accordingly, the invention provides a production process for isolating a protein of interest. In the process, a host cell (e.g., a yeast or fungus), into which has been introduced both a nucleic acid encoding a transactivator fusion protein of the invention and a nucleic acid encoding the protein of the interest operatively linked to at least one tet operator sequence, is grown at production scale in a culture medium in the presence of tetracycline or a tetracycline analogue to stimulate transcription of the nucleotides sequence encoding the protein of interest (i.e., the nucleotide sequence operatively linked to the tet operator sequence(s)) and the protein of interest is isolated from harvested host cells or from the culture medium. Standard protein purification techniques can be used to isolate the protein of interest from the medium or from the harvested cells.

C. Production of Proteins in Vivo

The invention also provides for large scale production of a protein of interest in animals, such as in transgenic farm animals. Advances in transgenic technology have made it possible to produce transgenic livestock, such as cattle, goats, pigs and sheep (reviewed in Wall, R. J. et al. (1992) *J. Cell. Biochem.* 49:113–120; and Clark, A. J. et al. (1987) *Trends in Biotechnology* 5:20–24). Accordingly, transgenic livestock carrying in their genome the components of the inducible regulatory system of the invention can be constructed, wherein a gene encoding a protein of interest is operatively linked to at least one tet operator sequence. Gene expression, and thus protein production, is induced by administering Tc (or analogue thereof) to the transgenic animal. Protein production can be targeted to a particular tissue by linking the nucleic acid encoding the transactivator fusion protein to an appropriate tissue-specific regulatory element(s) which limits expression of the transactivator to certain cells. For example, a mammary gland-specific regulatory element, such as the milk whey promoter (U.S. Pat. No. 4,873,316 and European Application Publication No. 264,166), can be linked to the transactivator transgene to limit expression of the transactivator to mammary tissue. Thus, in the presence of Tc (or analogue), the protein of interest will be produced in the mammary tissue of the transgenic animal. The protein can be designed to be secreted into the milk of the transgenic animal, and if desired, the protein can then be isolated from the milk.

D. Animal Models of Human Disease

The transcriptional activator proteins of the invention can be used to stimulate expression of specific genes in animals to mimic the pathophysiology of human disease to thereby create animal models of human disease. For example, in a host animal, a gene of interest thought to be involved in a disease can be placed under the transcriptional control of one or more tet operator sequences (e.g., by homologous recombination, as described herein). Such an animal can be mated to a second animal carrying a transgene for a transactivator fusion protein to create progeny that carry both a tetracycline-regulated fusion protein(s) gene and a tet-regulated target sequence. Expression of the gene of interest in these progeny can be modulated using tetracycline (or analogue).

EXEMPLIFICATION

The present invention is further illustrated by the following examples which should not be construed as limiting in any way. The contents of all cited references, including literature references, issued patents, published patent applications as cited throughout this application are hereby expressly incorporated by reference. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No: 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I–IV (D. M. Weir and C. C. Blackwell, eds., 1986); Manipulating the Mouse Embryo, (Cold Spring Harbor Laboratory Press, Cold Spring Harbor, N.Y., 1986).

Specific materials and methods used in the following examples are described below:

Oligonucleotides Encoding Minimal Activation Domains

The minimal activation domains of this study were derived from VP16 and comprise position 436 to 447 according to Seipel, K., Georgiev, O., and Schaffnier, W. (1992) *EMBO J* 11, 4961–4968. Synthetic oligonucleotides encoding this domain and variations thereof were designated [F], [GF], [FG], [GG] and [Y], respectively, whereby the letters designate the amino acids at position 442. (triplets underlined). The sequences of the coding strands are shown below (with the triplets corresponding to the codon of position 442 underlined). The oligonucleotides encode one or two minimal domains as indicated by the letters in parentheses.

The protruding 5' ends of the double stranded oligonucleotides are compatible with the cleavage site of restriction endonuclease XmaI.

Plasmids

The ColE1-based plasmid pUHD141-1 (Kistner, A. (1992) Diploma Thesis, Univ. Heidelberg) contains the TetR coding sequence which is optimized at the 5' end for efficient initiation of translation (Kozak, M. (1983) *Microbiol Rev* 47, 1–45). Transcription of the tetR gene is controlled by the human cytomegalovirus IE promoter (Boshart, M. et al. (1985) *Cell* 41, 521–530). To allow insertion of DNA in frame with the 3' end of the tetR open reading frame via XmaI cleavage, pUHD141-1 was linearized with Afl II which overlaps the tetR stop codon. Protruding 5' DNA ends were removed by mung bean nuclease and the synthetic oligonucleotide 5'-CCCGGGTAACTAAGTAA-3' (SEQ ID NO: 14) was ligated into the vector using standard cloning procedures. The resulting plasmid pUHD141-1/X containing a XmaI cleavage site at the very 3' end of the tetR gene was verified by sequence analysis.

Cell Culture and Transient Transfections

HeLa X1/6 cells containing chromosomally integrated copies of the luciferase reporter construct pUHC13-3 (Gossen, M. (1993) Ph. D. Thesis, Univ. Heidelberg) and HeLa (wt) cells were maintained at 37° C. and 5% $CO_2$ in Earl's modified Eagles medium (E-MEM from GIBCO) supplemented with 10% fetal calf serum. Transfections by calcium-phosphate coprecipitation were performed according to standard protocols with the following modifications: HeLa X1/6 cells were grown in 35 mm dishes to 50–60% confluency. 1 h prior to transfection, the culture medium was renewed and the cells were incubated at 37° C. and 6% $CO_2$. The calcium-phosphate/DNA precipitate contains 1.5 μg of plasmid DNA (consisting of 0.5 μg of the transactivator construct, 0.4 μg of a lacZ expression vector (pUHD16-1) included for normalization of transfection efficiency and 0.6 μg pUC18 as unspecific carrier DNA). The precipitate (100 μl per dish) was added to X1/6 cells which were then further incubated at 37° C. and 6% $CO_2$ for 30 h. Transfection efficiency as determined by in situ β-galactosidase staining of parallel cultures was between 60 and 80%.

Luciferase Assay 35 mm dishes containing transfected X1/6 cells were washed with 3 ml phosphate buffered saline (PBS) and lysed in 125 μl lysis buffer containing 25 mM Tris-phosphate pH 7.8, 2 mM dithiothreitol, 2 mM diaminocyclohexanetetraacetic acid, 10% glycerol and 1% Triton X-100 for 10 min at room temperature. The lysates were scraped off the dishes and centrifuged for 10 sec in an Eppendorf centrifuge. Luciferase activity in these extracts was measured as described in (Gossen, M., and Bujard, H. (1992) *Proc. Natl. Acad. Sci. U.S.A.* 89, 5547–5551) and luciferase values were normalized to β-galactosidase activity by performing standard liquid O-nitrophenyl β-galactopyranoside assay

```
Oligo [F]:   5'-CCGGCCGACGCCCTGGACGACTTCGACCTGGACATGCTG-3'(SEQ ID NO: 9)

Oligo [GF]:  5'-CCGGCCGACGCCCTGGACGACGGCGACCTGGACATGCTGCC (SEQ ID NO: 10)
             TGCTGATGCTCTCGATGATTTCGATCTCGATATGCTCC-3'

Oligo [FG]:  5'-CCGGCCGACGCCCTGGACGACTTCGACCTGGACATGCTGCC (SEQ ID NO: 11)
             TGCTGATGCTCTCGATGATGGCGATCTCGATATGCTCC-3'

Oligo [GG]:  5'-CCGGCCGACGCCCTGGACGACGGCGACCTGGACATGCTGCC (SEQ ID NO: 12)
             TGCTGATGCTCTCGATGATGGCGATCTCGATATGCTCC-3'

Oligo [Y]:   5'-CCGGCCGACGCCCTGGACGACTACGACCTGGACATCCTC-3'(SEQ ID NO: 13)
```

(Miller, J. H. (1972) *Experiments in Molecular Genetics*. Cold Spring Harbor Laboratory Press, Cold Spring Harbor).

DNA Retardation-Assay

HeLa cells were grown in 10 cm dishes to 50–60% confluency and transfected via the calcium phosphate procedure with 20 μg of plasmid DNA encoding the various tTAs. 30 h post transfection total cell extracts were prepared as follows: cells (approx. 2×10$^6$) were washed with PBS, centrifuged, resuspended in 250 μl of a buffer containing 10 mM HEPES, 1.5 mM MgCl$_2$, 10 mM KCl, 0.5 mM dithiothreitol and 1 mM phenylmethylsulfonyl fluoride and incubated for 20 min at 0° C. before they were quickly frozen and thawed. NaCl was added to a final concentration of 250 mM and after incubation for 20 min at 0° C., the samples were centrifuged in a Beckman TL-100 ultracentrifuge at 435 000 g and 0° C. for 10 min. Aliquots of the extracts (10 μl) were mixed with 10 μl of binding buffer (20 mM MgCl$_2$, 20 mM Tris pH 7.5, 10% glycerol, 2 mg/ml of herring sperm DNA and 1 mg/ml of bovine serum albumin) and 2 fmol of $^{32}$P-labelled tetO DNA isolated from pUHC13-3 (Gossen, M., and Bujard, H. (1992) *Proc. Natl. Acad. Sci. U.S.A.* 89, 5547–5551) as a 42 base pair TaqI fragment after filling in the protruding ends with T4-DNA polymerase in the presence of [α-$^{32}$P] dCTP. After 25 min, the reaction mixture was loaded onto a 5% polyacrylamide/0.13% bisacrylamide gel containing 5% glycerol. Electrophoresis was carried out in 45 mM Tris base, 45 mM boric acid and 1 mM EDTA at 7 V/cm.

Generation of Stably Transfected Cell Lines

HeLa X1/6 cells were grown in 35 mm dishes and transfected with 2 μg linearized plasmid DNA as described above. The transfection mixture contained plasmid pHMR272 (Bernard, H. U. et al. (1985) *Exp. Cell Res.* 158, 237–243) carrying the hygromycin gene and plasmids pUHD15-1, pUHD19-1 or pUHD26-1 (containing the Kozak sequence upstream of the tTA gene), respectively. The molar ratio between the plasmid in question and the selection marker was 40:1. After 24 h, cells were transferred into 10 cm dishes and maintained in medium containing 300 μg/ml hygromycin. Resistant clones were isolated, expanded separately and analyzed for luciferase activity (Gossen, M., and Bujard, H. (1992) *Proc. Natl. Acad. Sci. U.S.A.* 89, 5547–5551). To further investigate tTA-dependent activation ofthe luciferase gene in those clones, cells were seeded at a density of 10 000 cells per 35 mm dish and grown in the presence or absence of Tc (1 μg/ml). After 5 days, cell extracts were prepared as described above and luciferase activity was measured. The protein content of the lysates was determined according to Bradford (Bradford, M. M. (1976) *Anal Biochem* 72, 248–254).

Generation of Cell Pools Stably Expressing Various Transactivators and Quantitation of Relative Intracellular tTA Concentrations Plasmids pUHD15-1, pUHD19-1, pUHD20-1 and pUHD26-1 were modified by inserting a selectable marker gene. In each case, an expression cassette containing the neo gene was inserted into the XhoI site located upstream of PhCMv (1). The resulting plasmids were designated pUHD15-1neo, pUHD19-1neo, pUHD20-1neo and pUHD26-1neo, respectively.

HeLa cells were grown in 10 cm dishes to 50% confluency and transfected with 20 μg linearized plasmid DNA as described above. After 24 hours, cells were transferred into 14.5 cm dishes and maintained in medium containing 500 μg/ml G418. Resistant clones were then pooled, seeded into 14.5 cm dishes and grown under selective pressure until they reached confluency. Extracts from cell pools were prepared and DNA retardation assays were carried out as described above. Total protein content of the extracts was determined according to Bradford (Bradford, M. M. (1976) *Anal Biochem* 72, 248–254). Protein-DNA complexes were detected and quantified by a phosphorimager. In all HeLa cell extracts, a protein with some affinity to tet operator DNA is observed. This protein marked with an asterisk (FIG. 3A) was used as an internal marker for the quantitation of the various transactivators.

EXAMPLE 1

Construction of Fusions between TetR and Minimal Activation Domains Derived From VP16

VP16 contains two distinct transcriptional activation domains characterized by bulky, hydrophobic amino acids positioned in a highly negatively charged surrounding (Regier, J. L., Shen, F., and Triezenberg, S. J. (1993) *Proc. Natl. Acad. Sci. U.S.A.* 90, 883–887). Each domain was shown to activate transcription when fused to a heterologous DNA binding domain, such as the one of GAL4 (Seipel, K., Georgiev, O., and Schaffner, W. (1992) *EMBO-J* 11, 4961–4968). An oligonucleotide [F] encoding the acidic domain delineated by position 436 to 447 (the amino acid sequence of which is shown in SEQ ID NO: 1) was synthesized and inserted into plasmid pUHD141-1/X in frame with the 3' end of the tetR gene. Due to multiple integrations, sequences were generated which encode transactivators containing 1, 2, 3 or 4 activation modules. They were designated as TetR-F, TetR-FF, TetR-FFF, TetR-FFFF, respectively. The structures of these constructs are shown schematically in FIG. 1. To reduce possible structural constraints induced by the repeat units, the individual domains were joined by a proline which also connects the first domain to TetR. Each transactivator construct was verified by sequence analysis.

To broaden the range of the activation potential of fusions between TetR and VP 16 derived minimal domains, the sequence of the latter was varied by replacing Phe with Gly or Tyr, respectively. Several TetR fusions containing various combinations of mutated (G, Y) and wild type (F) domains were generated and are shown schematically in FIG. 1. For simplicity, the TetR fusions capable of activating transcription are designated tTA1 through tTA7 as indicated in Table 1 (see Example 3).

EXAMPLE 2

Tc-Dependent Binding of the Novel TetR Fusion Proteins to tetO Sequences

Figure 2A:
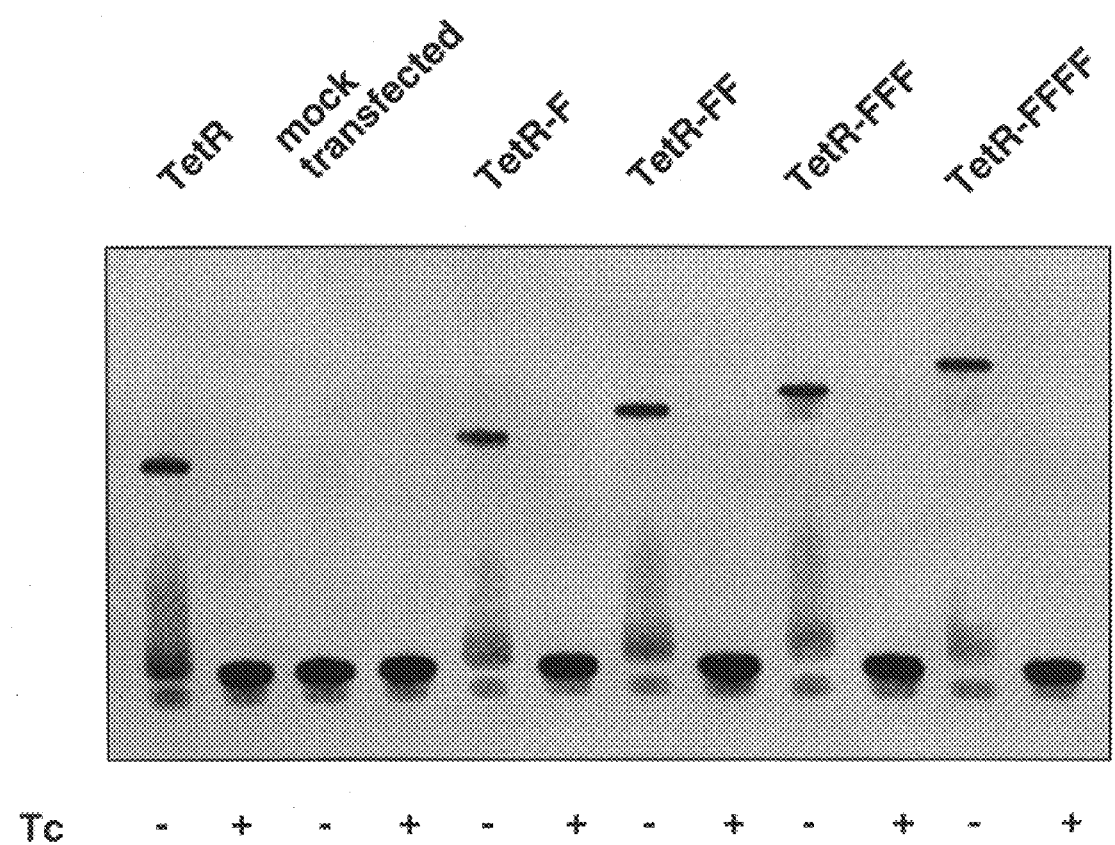
FIGS. 2A and 2B are photographs of electrophoretic mobility shift assays characterizing the various TetR fusions. HeLa cells grown in 10 cm dishes to 40% confluency were transiently transfected with plasmid DNA encoding either TetR or one of the fusion proteins shown in FIG. 1. Cell extracts prepared after 36 h were combined with radio labelled tetO DNA in the presence or absence of tetracycline. Protein-DNA complexes were separated electrophoretically and detected by using a phosphor imager.

Binding of the new TetR chimeras to tetO was examined by DNA retardation experiments. The various proteins were produced by transient expression of plasmids pUHD141-1/X and pUHD18-1 through pUHD21-1 in HeLa cells. 30 h after transfection, extracts were prepared and incubated with radiolabeled tetO DNA. Electrophoretic separation of the protein-DNA complexes shows that the new fusion proteins bind tetO DNA with an efficiency comparable to that of TetR (see FIG. 2A) and form complexes which migrate according to the molecular weight of the respective fusion proteins. Presence of Tc in the binding assay prevents complex formation. Furthermore this analysis suggests that the new fusion proteins are stable as no degradation products are detectable.

Figure 2B:
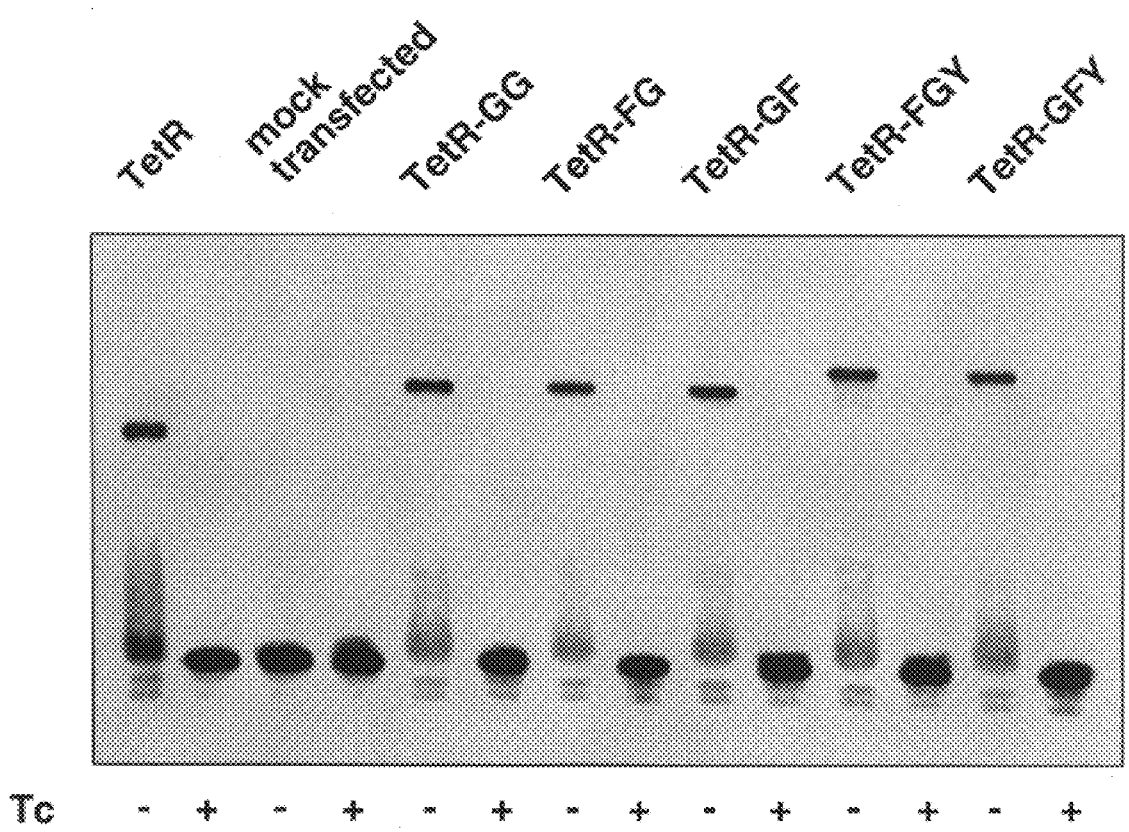

The TetR fusions containing mutant VP16 minimal activation domains were examined as well for their tetO binding. When produced in HeLa cells, all fusion proteins appear to efficiently bind tetO as evidenced by DNA retardation experiments (see FIG. 2B).

EXAMPLE 3

Activation Potential of TetR-[F] and Mutant Fusions

To assess the activation potential of the new TetR fusions, HeLa X1/6 cells were transiently transfected with plasmids encoding the respective proteins and luciferase activity determined. HeLa cell line X1/6, which contains the luciferase gene under transcriptional control of the tTA dependent promoter $P_{hCMV^*-1}$ (Gossen, M., and Bujard, H. (1992) *Proc. Natl. Acad. Sci. USA* 89, 5547–5551) chromosomally integrated, was grown in 35 mm dishes to 50% confluency. Cells were transiently transfected with DNA encoding either TetR or one of the new fusion proteins. Cultures were incubated in presence or absence of tetracycline (1 μg Tc/ml) for 30 h before luciferase activity was measured and standardized to β-galactosidase activity (introduced by cotransfection with pUHD16-1). The measurements of two independent transfection experiments are shown below in Table 1 and related to the activity of tTA (100%).

TABLE 1

| TetR Fusion | relative luciferase activity +Tc | relative luciferase activity −Tc | relative activation (%) | designation of transactivator | plasmid designation |
|---|---|---|---|---|---|
| TetR-VP16 | 20 | 265,410 | 100 | tTA | pUHD 15-1 |
| TetR | 26 | 32 | 0 | | pUHD 141-1/X |
| TetR-F | 21 | 21 | 0 | | pUHD 18-1 |
| TetR-FF | 27 | 102,828 | 39 | tTA3 | pUHD 19-1 |
| TetR-FFF | 33 | 259,556 | 98 | tTA2 | pUHD 20-1 |
| TetR-FFFF | 33 | 607,264 | 230 | tTA1 | pUHD 21-1 |
| TetR-GG | 28 | 30 | 0 | | pUHD 22-1 |
| TetR-FG | 24 | 88 | 0.03 | tTa7 | pUHD 23-1 |
| TetR-GF | 28 | 1,500 | 0.6 | tTA6 | pUHD 24-1 |
| TetR-FGY | 16 | 12,080 | 4.6 | tTA5 | pUHD 25-1 |
| TetR-GFY | 25 | 37,217 | 14 | tTA4 | pUHD 26-1 |

Luciferase activity in the HeLa X1/6 cell line is barely detectable but can be highly increased by transient expression of a tTA encoding gene; this activity is abolished by Tc (Table 1). The induction of the luciferase gene is entirely dependent on the activation domain fused to TetR as TetR alone has no effect (Table 1).

When the different TetR-[F] fusions were examined in this assay, a gradual increase in luciferase activity is observed whereby TetR-FF reaches about 40%, TetR-FFF almost 100% and TetR-FFFF about 230% of the activity conferred by tTA.

Interestingly, TetR-F containing a single minimal domain does not activate under these conditions.

When the activation potential of the mutant VP16 fusions was analyzed, essentially no activity was found for TetR-GG. However, by combining a [G]- with a [F]-domain, low but distinct activation is monitored amounting to about 0.03% (TetR-FG) and 0.6% (TetR-GF) of the activation potential of tTA, respectively. Higher levels of activation are conferred by the combination FGY and GFY which correspond to 4.6% and 14% of the tTA activity. Together with the [F]-domain containing TetR fusions described above, these combinations establish a panel of Tc-controlled transactivators which covers a range of activation strength of more than 3 orders of magnitude.

EXAMPLE 4

Control of Luciferase Activity in HeLa X1/6 Cells Constitutively Producing tTA3 and tTA4

To characterize the properties of some of the novel transactivators in stably transfected cells, the genes encoding tTA, tTA3 or tTA4 controlled by PhCMV were transferred into HeLa X1/6 cells. Cotransfection with pUHD19-1 or pUHD26-1 (Table 1) and pHMR272, which conveys hygromycin resistance (Bernard, H. U. et al. (1985) *Exp. Cell. Res* 158, 237–243), led to the isolation of resistant clones which were examined for luciferase activity in presence and absence of Tc. Cells of four clones selected for efficient regulation were seeded at a density of 10,000 cells/35 mm dish and grown in the presence or absence of tetracycline (1 μg/ml) for 5 days. The results are summarized below in Table 2. Values given are arithmetic means of 5 independent cultures.

TABLE 2

| Cell Line | luciferase activity (rlu/μg of protein) +Tc | luciferase activity (rlu/μg of protein) −Tc | Regulation Factor |
|---|---|---|---|
| X1/6 * tTA (clone #1) | 4 (±0.2) | 1,062,283 (±44,221) | ~2.5 × $10^5$ |
| X1/6 * tTA3 (clone #1) | 1 (±0.3) | 228,363 (±015,608) | ~2.2 × $10^5$ |
| X1/6 * tTA3 (clone #3) | 3 (±0.1) | 462,184 (±21,585) | ~1.5 × $10^5$ |
| X1/6 * tTA4 (clone #7) | 2 (±0.2) | 89,010 (±3,220) | ~4.4 × $10^4$ |
| X1/6 | 1 (±0.2) | 1 (±0.4) | — |

In the resistant clones, luciferase activity in presence of Tc is indistinguishable from the activity of non-transfected X1/6 cells (Table 2), whereas in the absence of the effector, it can be stimulated more than $10^4$ fold. These data confirm the functionality of the two new transactivators tTA3 and tTA4 under stable cellular conditions. They both allow to tightly regulate transcription via a tTA/rtTA responsive promoter. It should be emphasized that in the clones tested, the level of activation conveyed by TetR-FF and TetR-GFY cannot be compared with the data obtained in transient transfections (Table 1). In the latter experiments, the same amount of transactivator encoding DNA was introduced into the cells resulting in comparable intracellular concentrations of the tTA proteins. Therefore, the different levels of activation reflect the properties of the respective TetR fusion. By contrast, in stably transfected cells, the genes encoding the transactivators are randomly integrated into the genome. Their expression is both copy number and locus dependent and consequently, their intracellular concentration will differ from clone to clone. These concentration differences rather than the properties of the respective transactivators are thus reflected by the different levels of activation.

EXAMPLE 5

Intracellular Concentrations of Transactivators

Figure 3A:
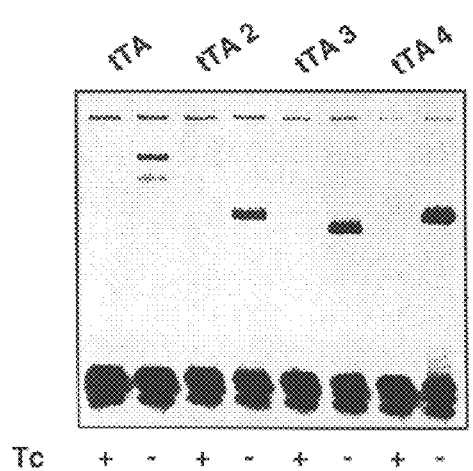
FIGS. 3A and 3B are photographs of electrophoretic mobility shift assays comparing intracellular concentrations of transactivators. Protein extracts prepared from cells stably expressing various transactivators were subjected to electrophoretic mobility shift assays with radioactively labelled tet operator DNA. Protein and DNA were mixed in presence or in absence of tetracycline (+Tc) before comparable amounts were applied to the polyacrylamide gel.
Figure 3B:
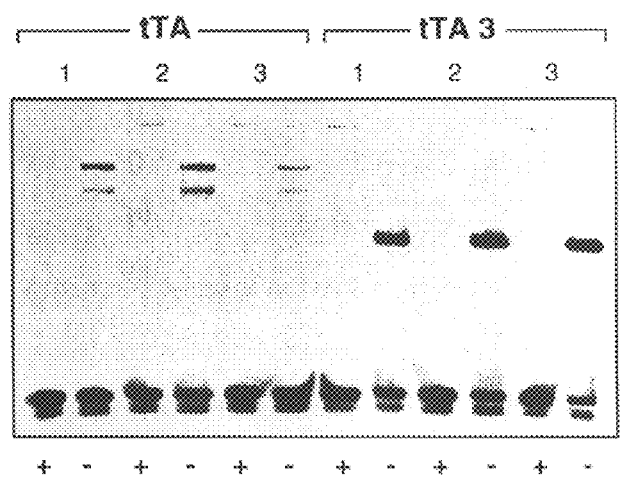

To examine whether transactivators with minimal domains are tolerated at higher intracellular concentrations than tTA, HeLa cells were transfected in parallel with plasmids encoding tTA, tTA2, tTA3 and tTA4, respectively. The corresponding plasmids (Table 1) were equipped with a neo resistance marker (see Method section above) to ensure that clones resistant to G418 would also express the transactivator gene. Selection for G418 resistance led to pools of 300 to 500 colonies. Such pools were grown up and protein extracts were analyzed for transactivator protein by electrophoretic mobility shift experiments with radioactively-labelled tet operator DNA. As shown in FIG. 3A, all transactivators consisting of TetR and minimal activation domains are present in the cell at higher concentrations than the TetR-VP16 fusion protein tTA. Interestingly, tTA2 which has the same activation potential as tTA (Table 1) is nevertheless tolerated at a three fold higher concentration. Among the new transactivators, however, the intracellular concentration increases inversely with the respective activation potential. Thus, tTA3 and tTA4 concentrations are 5 and 9 fold higher, respectively, than that of tTA. When individual clones producing either tTA or tTA3 were analyzed for the relative abundance of the transactivators, again by DNA retardation assays, the same picture emerged: the intracellular concentration of tTA3 was again about 5 times higher than that of tTA (FIG. 3 B). Extracts from HeLa cells expressing tTA show a second protein-DNA complex in the DNA retardation assay which appears to be a degradation product of tTA (FIG. 3). This product is found to variable extent also in other cell lines. From the mobility of this complex, it can be estimated that around 42 amino acids have been cleaved off, most likely from the C-terminus, since a deletion of this size from the N-terminus would abolish the operator binding capacity of the transactivator. Therefore, this degradation product has most likely lost the second (C-terminal) activation domain of the VP16 moiety. It is not clear whether such a truncated protein will still act as a transactivator.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated nucleic acid molecule encoding a fusion protein which activates transcription, the fusion protein comprising a first polypeptide comprising a DNA binding domain operatively linked to a second polypeptide comprising a transcriptional activation domain, wherein the transcriptional activation domain comprises at least one copy of a mutated acidic region of herpes simplex virus virion protein 16 (HSV VP16), the mutated acidic region consisting of amino acid positions 436 to 447 of HSV VP16 (SEQ ID NO: 1) and having an amino acid substitution at position 442 as compared to wild type HSV VP16.

2. The nucleic acid molecule of claim 1, wherein the mutated acidic region of HSV VP16 has the amino acid sequence of SEQ ID NO: 2.

3. The nucleic acid molecule of claim 1, wherein the mutated acidic region of HSV VP16 has the amino acid sequence of SEQ ID NO: 3.

4. The nucleic acid molecule of claim 1, wherein the transcriptional activation domain comprises the amino acid sequence of SEQ ID NO: 4.

5. The nucleic acid molecule of claim 1, wherein the transcriptional activation domain comprises the amino acid sequence of SEQ ID NO: 5.

6. The nucleic acid molecule of claim 1, wherein the transcriptional activation domain comprises the amino acid sequence of SEQ ID NO: 6.

7. The nucleic acid molecule of claim 1, wherein the transcriptional activation domain comprises the amino acid sequence of SEQ ID NO: 7.

8. The nucleic acid molecule of claim 1, wherein the transcriptional activation domain comprises the amino acid sequence of SEQ ID NO: 8.

9. The nucleic acid molecule of claim 1, wherein the first polypeptide is a Tet repressor.

10. The nucleic acid molecule of claim 1, wherein the first polypeptide is a mutated Tet repressor that binds to tetO sequences in the presence, but not in the absence, of tetracycline or a tetracycline analogue.

11. The nucleic acid molecule of claim 1, wherein the first polypeptide is selected from the group consisting of GAL4, LexA, LacR and steroid hormone receptors.

12. An isolated nucleic acid molecule encoding a fusion protein which activates transcription, the fusion protein comprising a first polypeptide comprising a DNA binding domain operatively linked to a second polypeptide comprising a transcriptional activation domain, wherein the transcriptional activation domain consists of three copies of an acidic region of herpes simplex virus virion protein 16 (HSV VP16), the acidic region consisting of amino acid positions 436 to 447 of HSV VP16 (SEQ ID NO:1).

13. The nucleic acid molecule of claim 12, wherein the first polypeptide is a Tet repressor.

14. The nucleic acid molecule of claim 12, wherein the first polypeptide is a mutated Tet repressor that binds to tetO sequences in the presence, but not in the absence, of tetracycline or a tetracycline analogue.

15. The nucleic acid molecule of claim 12, wherein the first polypeptide is selected from the group consisting of GAL4, LexA, LacR and steroid hormone receptors.

16. An isolated nucleic acid molecule encoding a fusion protein which activates transcription, the fusion protein comprising a first polypeptide comprising a DNA binding domain operatively linked to a second polypeptide comprising a transcriptional activation domain, wherein the transcriptional activation domain consists of four copies of an acidic region of herpes simplex virus virion protein 16 (HSV VP16), the acidic region consisting of amino acid positions 436 to 447 of HSV VP16 (SEQ ID NO:1).

17. The nucleic acid molecule of claim 16, wherein the first polypeptide is a Tet repressor.

18. The nucleic acid molecule of claim 16, wherein the first polypeptide is a mutated Tet repressor that binds to tetO sequences in the presence, but not in the absence, of tetracycline or a tetracycline analogue.

19. The nucleic acid molecule of claim 16, wherein the first polypeptide is selected from the group consisting of GAL4, LexA, LacR and steroid hormone receptors.

20. A recombinant vector comprising the nucleic acid molecule of claim 1 in a form suitable for expression of the fusion protein in a host cell.

21. A recombinant vector comprising the nucleic acid molecule of claim 12 in a form suitable for expression of the fusion protein in a host cell.

22. A recombinant vector comprising the nucleic acid molecule of claim 16 in a form suitable for expression of the fusion protein in a host cell.

23. A host cell comprising the vector of claim 20.
24. A host cell comprising the vector of claim 21.
25. A host cell comprising the vector of claim 22.

* * * * *

```
                         SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (xi) SEQUENCE DESCRIPTION: SEQ ID NO:1:

Ala Asp Ala Leu Asp Asp Phe Asp Leu Asp Met Leu
              5                  10

(2) INFORMATION FOR SEQ ID NO:2:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (xi) SEQUENCE DESCRIPTION: SEQ ID NO:2:

Ala Asp Ala Leu Asp Asp Gly Asp Leu Asp Met Leu
              5                  10

(2) INFORMATION FOR SEQ ID NO:3:

(i) SEQUENCE CHARACTERISTICS:
         (A) LENGTH: 12 amino acids
         (B) TYPE: amino acid
         (D) TOPOLOGY: linear (ii) MOLECULE TYPE: peptide (xi) SEQUENCE DESCRIPTION: SEQ ID NO:3:

Ala Asp Ala Leu Asp Asp Tyr Asp Leu Asp Met Leu
              5                  10
```

(2) INFORMATION FOR SEQ ID NO:4:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:4:

Ala Asp Ala Leu Asp Asp Gly Asp Leu Asp Met Leu Pro Ala Asp Ala
                 5                  10                  15

Leu Asp Asp Gly Asp Leu Asp Met Leu
            20                  25

(2) INFORMATION FOR SEQ ID NO:5:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:5:

Ala Asp Ala Leu Asp Asp Phe Asp Leu Asp Met Leu Pro Ala Asp Ala
                 5                  10                  15

Leu Asp Asp Gly Asp Leu Asp Met Leu
            20                  25

(2) INFORMATION FOR SEQ ID NO:6:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO:6:

Ala Asp Ala Leu Asp Asp Gly Asp Leu Asp Met Leu Pro Ala Asp Ala
                 5                  10                  15

Leu Asp Asp Phe Asp Leu Asp Met Leu
            20                  25

(2) INFORMATION FOR SEQ ID NO:7:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO:7:

Ala Asp Ala Leu Asp Asp Phe Asp Leu Asp Met Leu Pro Ala Asp Ala
                 5                  10                  15

Leu Asp Asp Gly Asp Leu Asp Met Leu Pro Ala Asp Ala Leu Asp Asp
            20                  25                  30

Tyr Asp Leu Asp Met Leu
    35

(2) INFORMATION FOR SEQ ID NO:8:

(i) SEQUENCE CHARACTERISTICS:
        (A) LENGTH: 38 amino acids
        (B) TYPE: amino acid
        (D) TOPOLOGY: linear (ii) MOLECULE TYPE: peptide (xi) SEQUENCE DESCRIPTION: SEQ ID NO:8:

Ala Asp Ala Leu Asp Asp Gly Asp Leu Asp Met Leu Pro Ala Asp Ala
             5                   10                15

Leu Asp Asp Phe Asp Leu Asp Met Leu Pro Ala Asp Ala Leu Asp Asp
          20                25              30

Tyr Asp Leu Asp Met Leu
        35

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:9:

CCGGCCGACG CCCTGGACGA CTTCGACCTG GACATGCTG                          39

(2) INFORMATION FOR SEQ ID NO:10:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:10:

CCGGCCGACG CCCTGGACGA CGGCGACCTG GACATGCTGC CTGCTGATGC TCTCGATGAT      60

TTCGATCTCG ATATGCTCC                                                                79

(2) INFORMATION FOR SEQ ID NO:11:

(i) SEQUENCE CHARACTERISTICS:
        (A) LENGTH: 79 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

CCGGCCGACG CCCTGGACGA CTTCGACCTG GACATGCTGC CTGCTGATGC TCTCGATGAT      60

GGCGATCTCG ATATGCTCC                                                                79

(2) INFORMATION FOR SEQ ID NO:12:

(i) SEQUENCE CHARACTERISTICS:
        (A) LENGTH: 79 base pairs
        (B) TYPE: nucleic acid
        (C) STRANDEDNESS: single
        (D) TOPOLOGY: linear -continued (ii) MOLECULE TYPE: oligonucleotide (xi) SEQUENCE DESCRIPTION: SEQ ID NO:12:

CCGGCCGACG CCCTGGACGA CGGCGACCTG GACATGCTGC CTGCTGATGC TCTCGATGAT        60

GGCGATCTCG ATATGCTCC        79

(2) INFORMATION FOR SEQ ID NO:13:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

CCGGCCGACG CCCTGGACGA CTACGACCTG GACATCCTC        39

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:14:

CCCGGGTAAC TAAGTAA        17